(12) United States Patent
Kim et al.

(10) Patent No.: US 7,935,486 B2
(45) Date of Patent: May 3, 2011

(54) KIT AND METHOD FOR QUANTITATIVELY DETECTING MULTIPLE PATHOGENIC MICROORGANISMS WITHOUT GENE AMPLIFICATION

(75) Inventors: Jae Man Kim, Gwangju (KR); Eui Chul Ro, Gwangju (KR)

(73) Assignees: Mokpo National University Industry-Academic Cooperation Foundation, Dorim-Ri, Cheonggye-Myeon, Jeollanam-Do, Muan-Gun (KR); Ro. Eui Chul, Wolgye-Dong, Gwangsan-Gu, Gwangju (KR)

( * ) Notice: Subject to any disclaimer, the term of this patent is extended or adjusted under 35 U.S.C. 154(b) by 68 days.

(21) Appl. No.: 12/296,933

(22) PCT Filed: Apr. 13, 2007

(86) PCT No.: PCT/KR2007/001820
§ 371 (c)(1),
(2), (4) Date: Oct. 12, 2008

(87) PCT Pub. No.: WO2007/119987
PCT Pub. Date: Oct. 25, 2007

(65) Prior Publication Data
US 2009/0325161 A1    Dec. 31, 2009

(30) Foreign Application Priority Data

Apr. 13, 2006    (KR) .................. 10-2006-0033554

(51) Int. Cl.
C12Q 1/68 (2006.01)
C07H 21/02 (2006.01)
C07H 21/04 (2006.01)
G01N 33/53 (2006.01)
C12P 19/34 (2006.01)

(52) U.S. Cl. ........... 435/6; 435/7.1; 435/91.2; 536/23.1; 536/24.3

(58) Field of Classification Search ............... 435/6, 7.1, 435/91.2; 536/23.1, 24.3
See application file for complete search history.

(56) References Cited

U.S. PATENT DOCUMENTS

| | | | |
|---|---|---|---|
| 4,740,467 A | | 4/1988 | Kettman et al. |
| 5,006,461 A | * | 4/1991 | Woiszwillo .................. 435/7.92 |
| 5,474,895 A | * | 12/1995 | Ishii et al. ........................ 435/6 |
| 5,550,040 A | * | 8/1996 | Purohit et al. .................... 435/6 |
| 5,719,923 A | | 2/1998 | Zarling et al. |
| 5,853,981 A | * | 12/1998 | Kondo et al. ..................... 435/5 |
| 2002/0010952 A1 | * | 1/2002 | Okada et al. .................. 800/287 |
| 2002/0119474 A1 | * | 8/2002 | Drazen et al. .................... 435/6 |
| 2003/0105307 A1 | * | 6/2003 | Sampson et al. ............. 536/23.1 |
| 2003/0124521 A1 | * | 7/2003 | Coull et al. ....................... 435/6 |
| 2003/0181379 A1 | * | 9/2003 | Econs et al. .................... 514/12 |
| 2004/0058389 A1 | * | 3/2004 | Wang et al. .................... 435/7.1 |
| 2004/0229268 A1 | * | 11/2004 | Hogan et al. ..................... 435/6 |
| 2005/0112752 A1 | * | 5/2005 | Polo et al. ...................... 435/239 |
| 2005/0289670 A1 | * | 12/2005 | Shi et al. ....................... 800/288 |
| 2006/0068403 A1 | * | 3/2006 | Chenchik et al. ................. 435/6 |
| 2009/0270602 A1 | * | 10/2009 | Coull et al. ................... 536/24.3 |
| 2010/0183656 A1 | * | 7/2010 | Ko et al. ..................... 424/190.1 |

FOREIGN PATENT DOCUMENTS

| | | |
|---|---|---|
| KR | 1020040055617 A | 6/2004 |
| KR | 100615420 B1 | 8/2006 |
| WO | WO2007/119987 A3 | 9/2007 |
| WO | WO2007/119987 A2 | 10/2007 |

OTHER PUBLICATIONS

Polsky-Cynkin et al., Use of DNA immobilized on plastic and agarose supports to detect DNA by sandwich hybridization. Clinical Chemistry 31 (9) : 1438-1443 (1985).*
Matthews et al. Review : Analytical Strategies for the use of DNA probes. Analytical Biochemistry 169 : 1-25 (1988).*
Thorpe et al. Phenols as enhancers of the chemiluminescent horseradish peroxidase- luminol-hydrogen peroxide reaction: application in luminescence- monitored enzyme immunoassays. Clinical Chemistry 31 (8) : 1335-1341 (1985).*
Machine Translation of Kim et al. Korean patent document 10-2006031068 (0033554).*

* cited by examiner

*Primary Examiner* — Ethan Whisenant
(74) *Attorney, Agent, or Firm* — Lexyoume IP Group, PLLC.

(57) ABSTRACT

A non-amplification multiple quantitative detection kit is characterized in that there are provided a single strand poly nucleotide having a base sequence designed to recognize a specific gene portion of a multiple pathogenic microorganisms to be detected by a fishing probe, and a double strand poly nucleotide indicated with a tag having a base sequence designed to recognize different gene portions which does not overlap with the recognition portion of the fishing probe in the specific genes of the multiple pathogenic microorganisms to be detected by a reporter probe.

18 Claims, 10 Drawing Sheets

[Fig1]
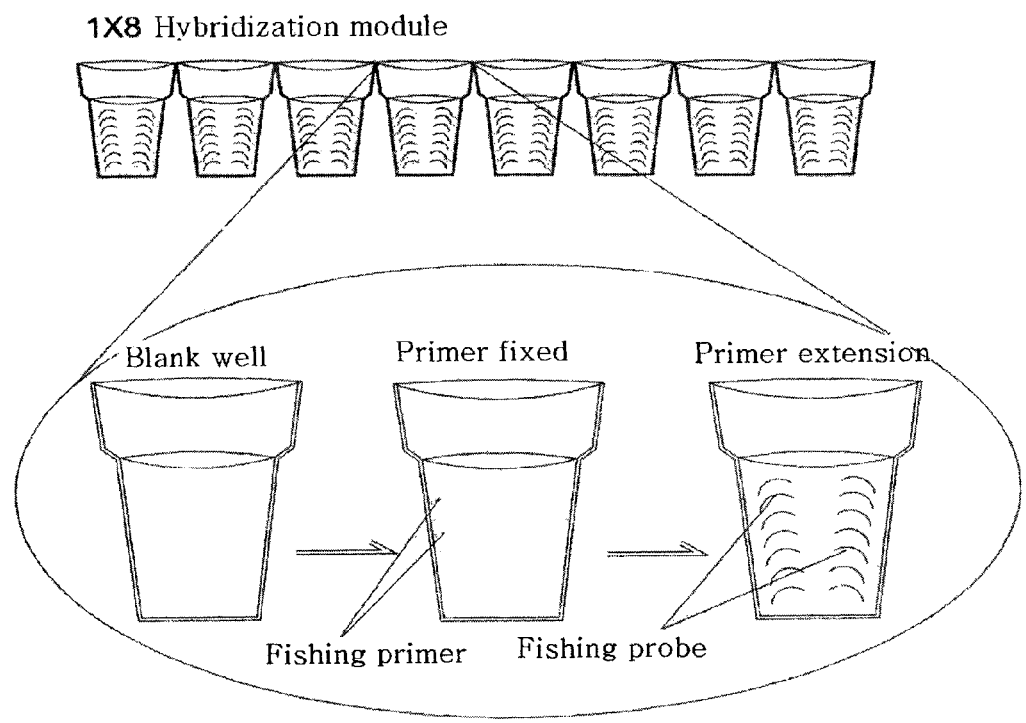
[Fig2]
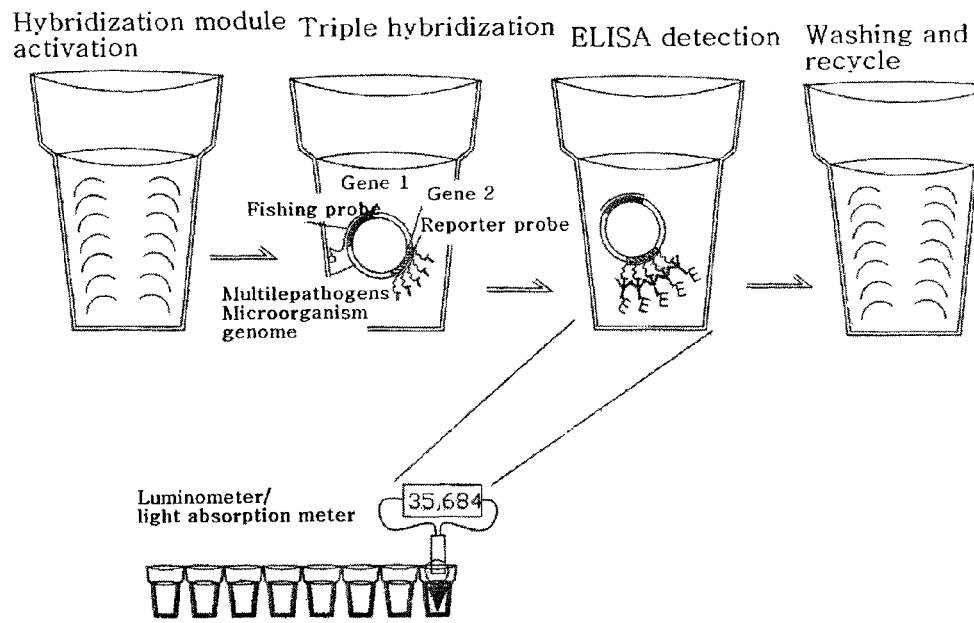

[Fig3]
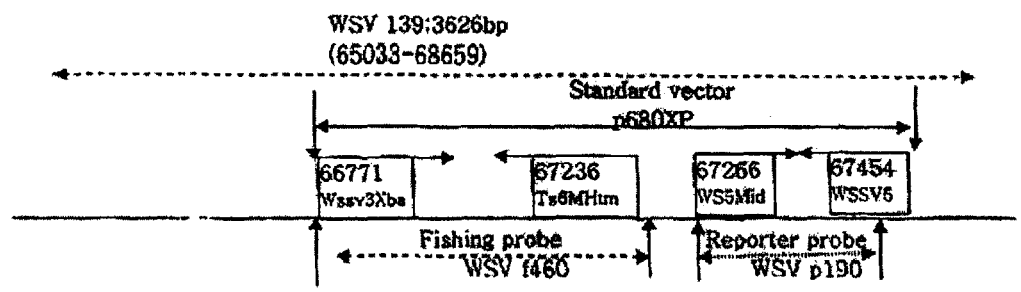
[Fig4]
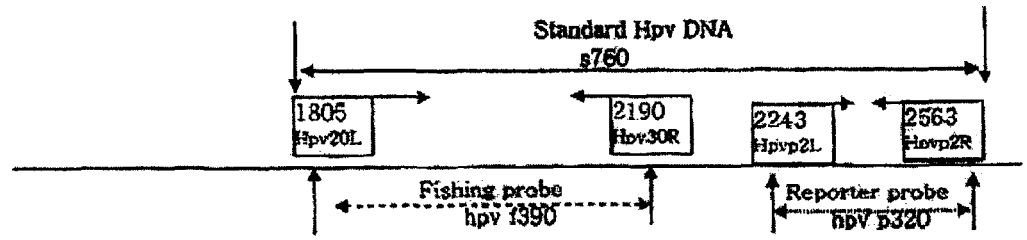

| | 1 | 2 | 3 | 4 | 5 | 6 | 7 | 8 | 9 | 10 | 11 | 12 |
|---|---|---|---|---|---|---|---|---|---|---|---|---|
| A | blk | blk | blk | blk | blk | blk | blk | blk | blk | blk | blk | blk |
| B | STa | STb | STa | STb | STa | STb | STa | STb | STa | STb | STa | STb |
| C | S1 | S1 | S1 | S1 | S1 | S1 | S1 | S1 | S1 | S1 | S1 | S1 |
| D | S2 | S2 | S2 | S2 | S2 | S2 | S2 | S2 | S2 | S2 | S2 | S2 |
| E | S3 | S3 | S3 | S3 | S3 | S3 | S3 | S3 | S3 | S3 | S3 | S3 |
| F | S4 | S4 | S4 | S4 | S4 | S4 | S4 | S4 | S4 | S4 | S4 | S4 |
| G | S5 | S5 | S5 | S5 | S5 | S5 | S5 | S5 | S5 | S5 | S5 | S5 |
| H | S6 | S6 | S6 | S6 | S6 | S6 | S6 | S6 | S6 | S6 | S6 | S6 |

(B)

| | 1 | 2 | 3 | 4 | 5 | 6 | 7 | 8 | 9 | 10 | 11 | 12 |
|---|---|---|---|---|---|---|---|---|---|---|---|---|
| A | blk | blk | blk | blk | blk | blk | blk | blk | blk | blk | blk | blk |
| B | STa | STb | STc | STd | STe | STf | STg | STh | STi | STj | STk | STl |
| C | S1 | S1 | S1 | S1 | S1 | S1 | S1 | S1 | S1 | S1 | S1 | S1 |
| D | S2 | S2 | S2 | S2 | S2 | S2 | S2 | S2 | S2 | S2 | S2 | S2 |
| E | S3 | S3 | S3 | S3 | S3 | S3 | S3 | S3 | S3 | S3 | S3 | S3 |
| F | S4 | S4 | S4 | S4 | S4 | S4 | S4 | S4 | S4 | S4 | S4 | S4 |
| G | S5 | S5 | S5 | S5 | S5 | S5 | S5 | S5 | S5 | S5 | S5 | S5 |
| H | S6 | S6 | S6 | S6 | S6 | S6 | S6 | S6 | S6 | S6 | S6 | S6 |

[Fig6]
| | 1 | 2 | 3 | 4 | 5 | 6 | 7 | 8 | 9 | 10 | 11 | 12 |
|---|---|---|---|---|---|---|---|---|---|---|---|---|
| A | blk | blk | blk | blk | blk | blk | blk | blk | blk | blk | blk | blk |
| B | STD1 | STD1 | STD1 | STD1 | STD1 | STD1 | STD1 | STD1 | STD1 | STD1 | STD1 | STD1 |
| C | STD2 | S1 | S1 | S1 | S1 | S1 | S1 | S1 | S1 | S1 | S1 | S1 |
| D | STD3 | S2 | S2 | S2 | S2 | S2 | S2 | S2 | S2 | S2 | S2 | S2 |
| E | STD4 | S3 | S3 | S3 | S3 | S3 | S3 | S3 | S3 | S3 | S3 | S3 |
| F | STD5 | S4 | S4 | S4 | S4 | S4 | S4 | S4 | S4 | S4 | S4 | S4 |
| G | STD6 | S5 | S5 | S5 | S5 | S5 | S5 | S5 | S5 | S5 | S5 | S5 |
| H | STD7 | S6 | S6 | S6 | S6 | S6 | S6 | S6 | S6 | S6 | S6 | S6 |
[Fig7]
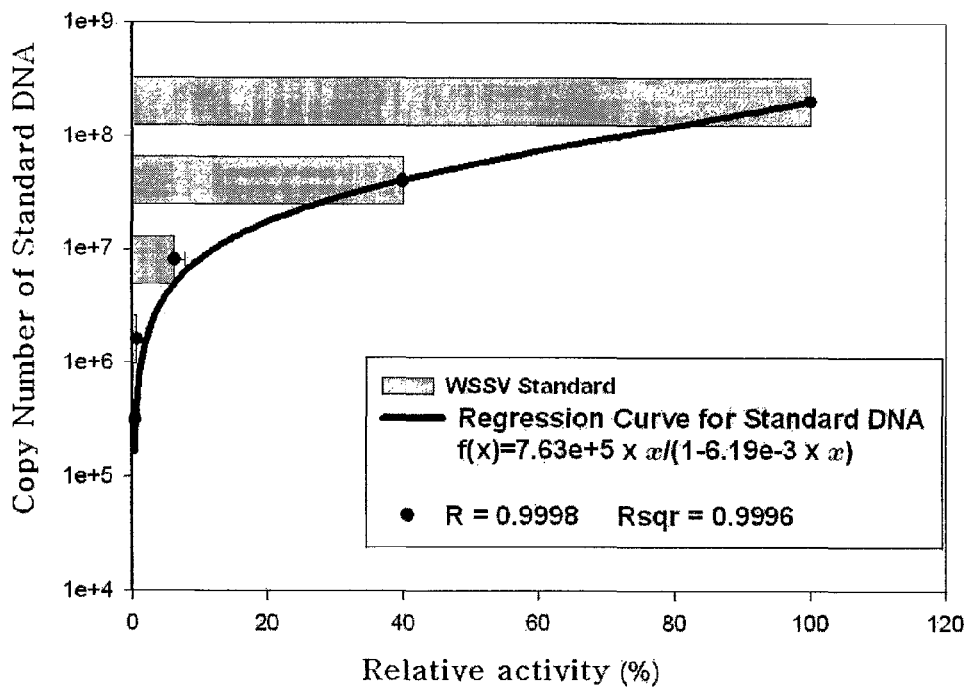

[Fig8]
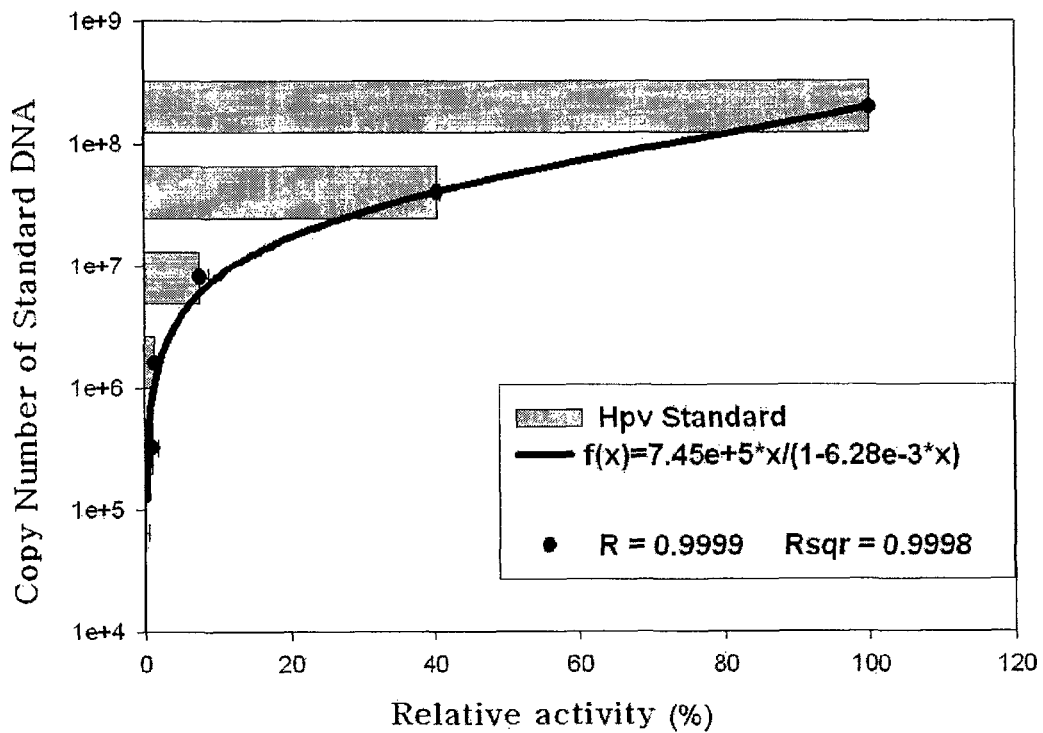
[Fig9]
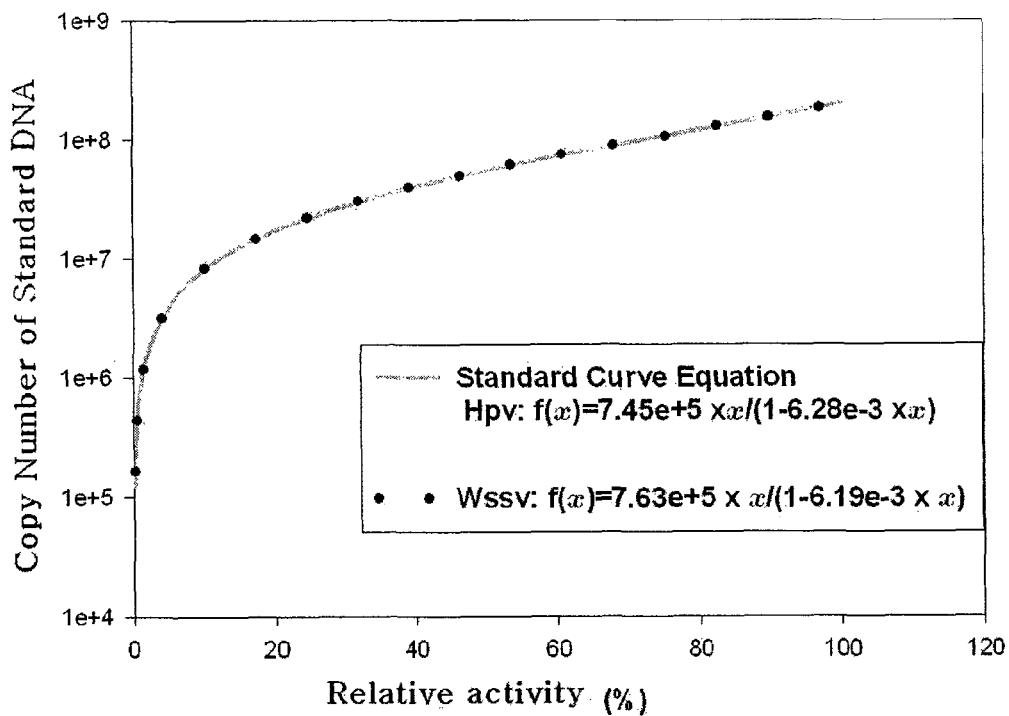

[Fig10]
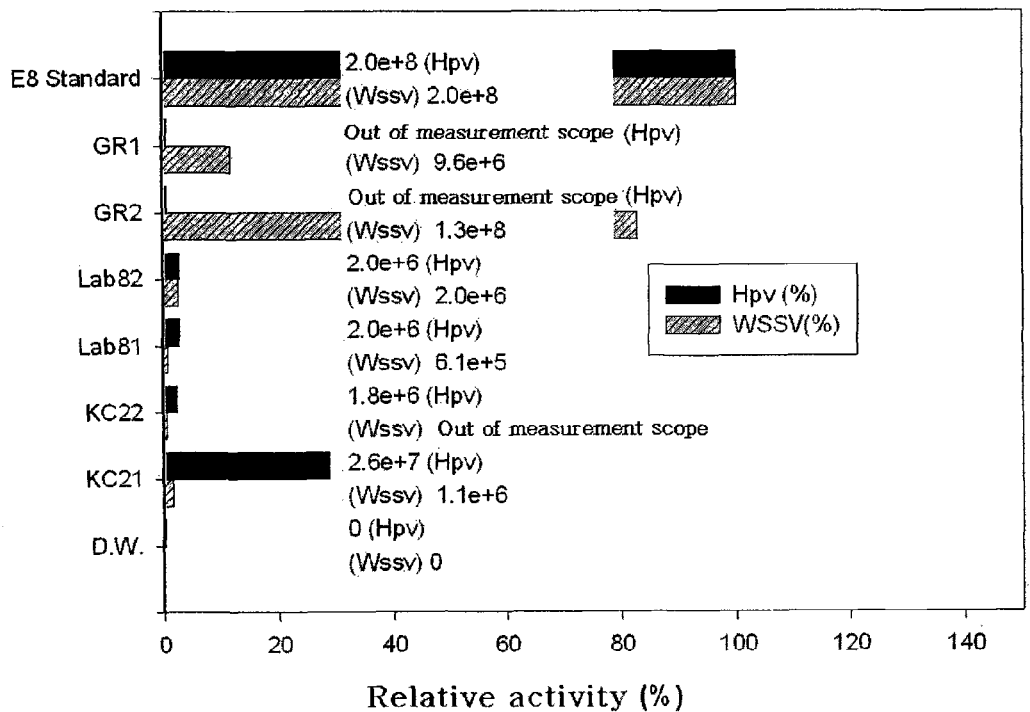
[Fig11]
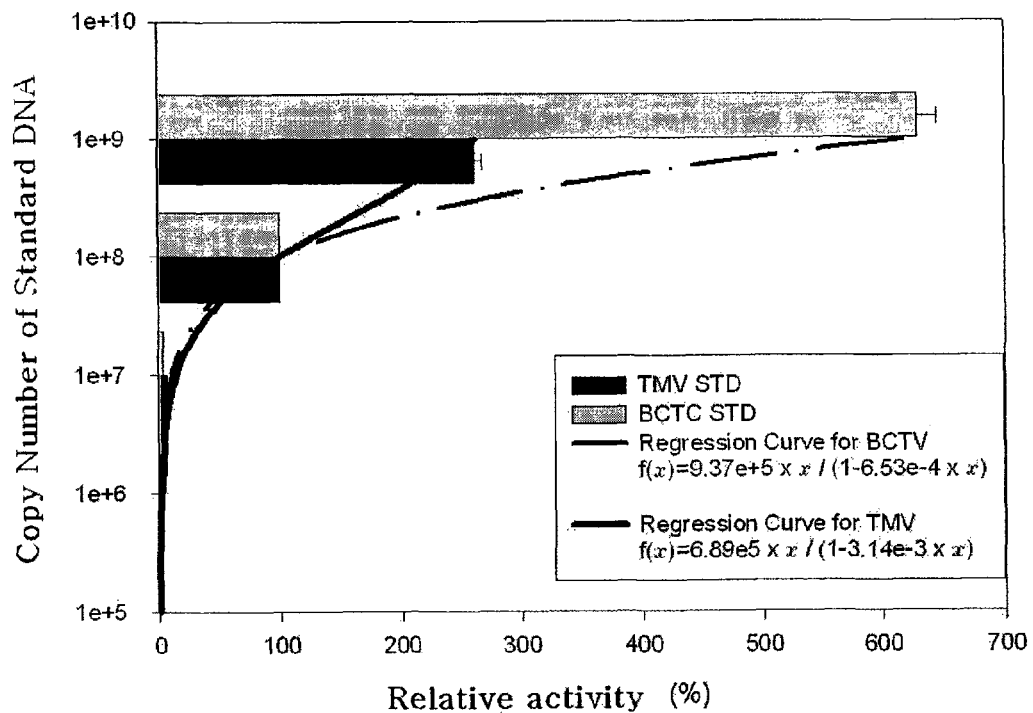

[Fig12]

TMV 1E+8 — TMV 1.00e+8 out of range BCTV
BCTV1 — TMV 9.27e+6  4.53e+7 BCTV
TMV1 — TMV 2.29e+7 out of range BCTV
Infection 1 high — TMV 2.18e+7  1.95e+6 BCTV
BCTV0928 — TMV out of range  1.59e+6 BCTV
BCTV1027 — TMV 6.28e+5 out of range BCTV
Infection 1 low — TMV 7.85e+6 out of range BCTV
BCTV 1E+8 — TMV out of range  1.00e+8 BCTV Legend: BCTV Module, TMV module Relative activity (%)

[Fig13]

Copy Number of Standard DNA vs Relative activity (%)

Standard DNA for RBIV MCP

Regression Curve for Standard DNA
$f(x) = 5.3e5 x^2 / (1 - 4.7e\text{-}3 x^2)$

[Fig14]
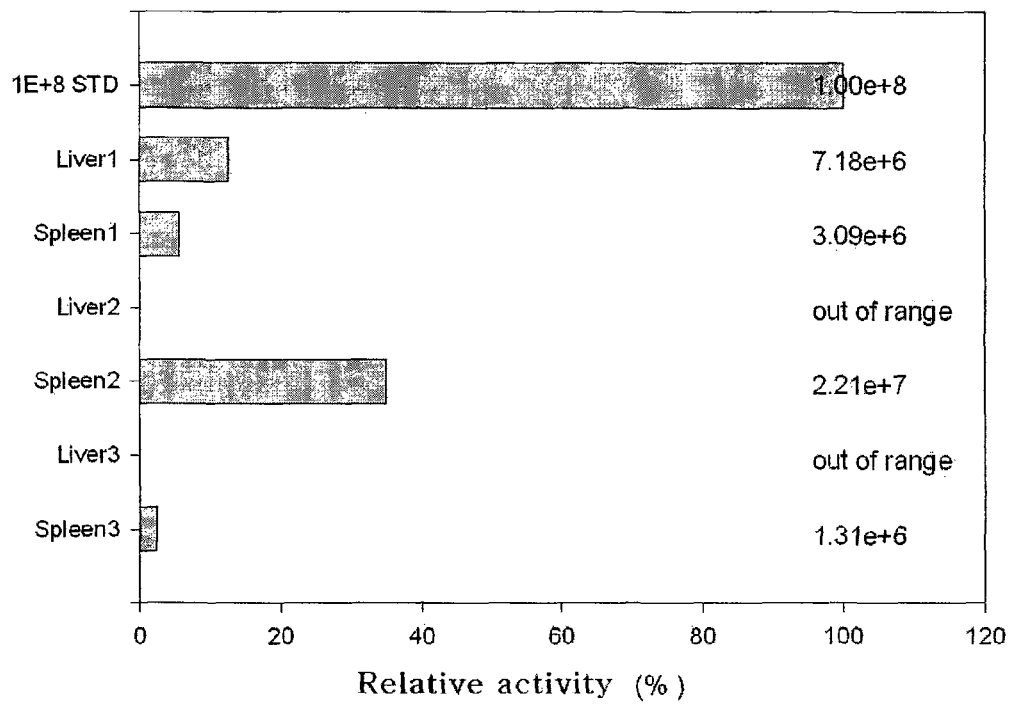
[Fig15]
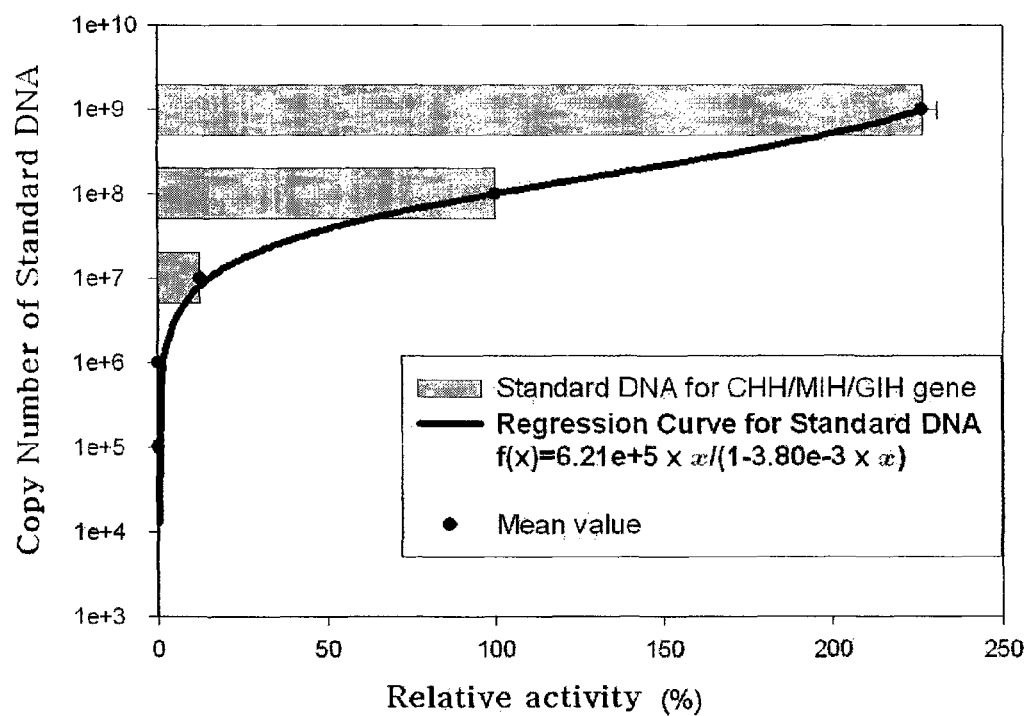

[Fig16]
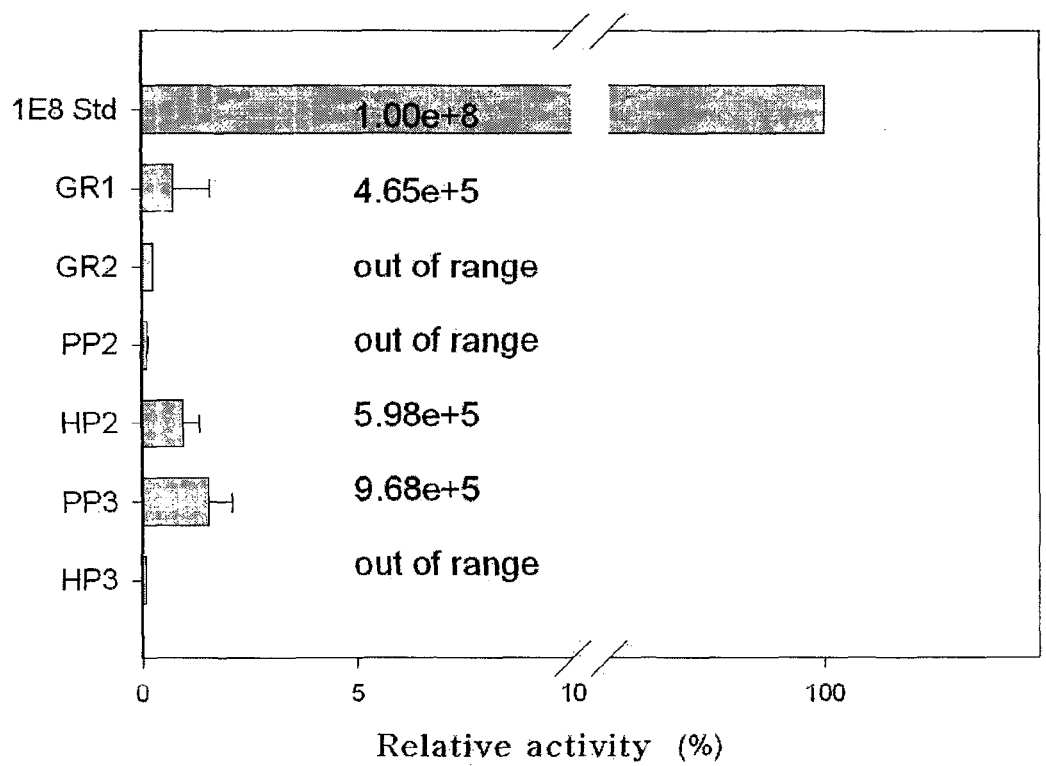

[Fig17]
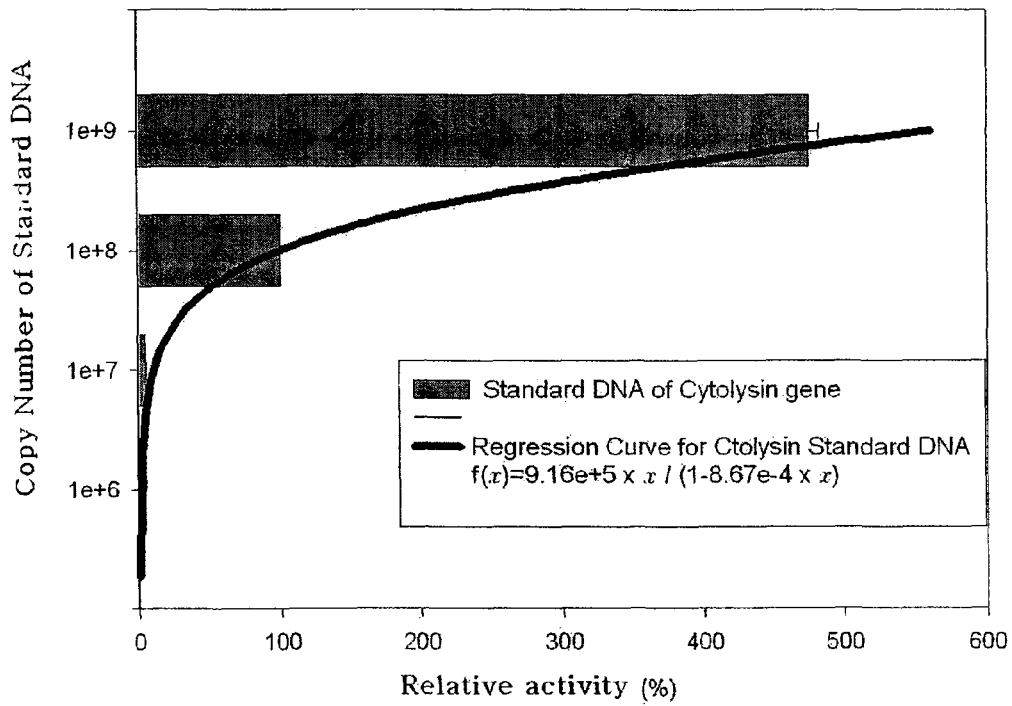
[Fig18]
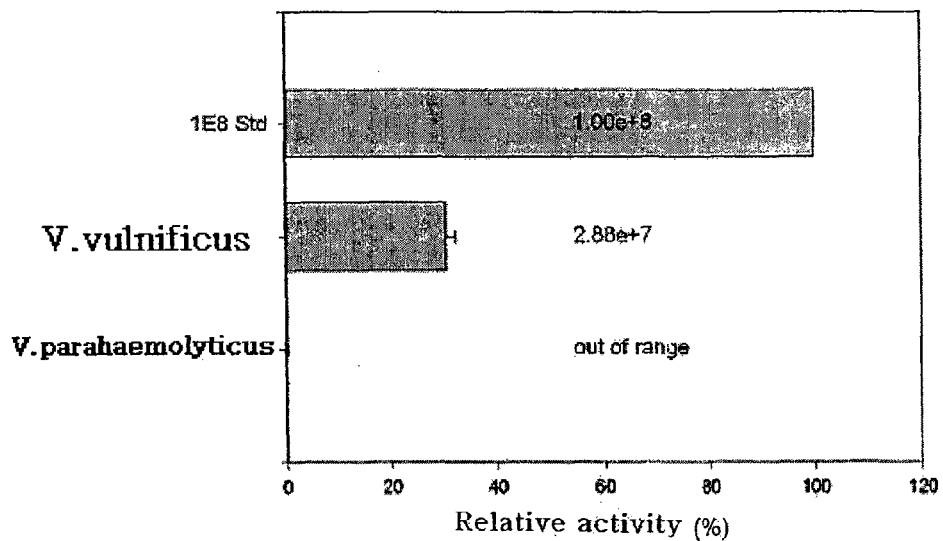

SEQUENCE LISTING

<160> NUMBER OF SEQ ID NOS: 48

<210> SEQ ID NO 1
<211> LENGTH: 30
<212> TYPE: DNA
<213> ORGANISM: Artificial Sequence
<220> FEATURE:
<223> OTHER INFORMATION: forward primer WSSV3Xba

<400> SEQUENCE: 1
tttttttttc tagaaatatt accaacacta                              30

<210> SEQ ID NO 2
<211> LENGTH: 30
<212> TYPE: DNA
<213> ORGANISM: Artificial Sequence
<220> FEATURE:
<223> OTHER INFORMATION: reverse primer Ts6MHtm
<220> FEATURE:
<221> NAME/KEY: misc_feature
<222> LOCATION: (1)
<223> OTHER INFORMATION: phosphorylated

<400> SEQUENCE: 2
cccacgattc tgatgtgctg gtgaaatgga                              30

<210> SEQ ID NO 3
<211> LENGTH: 475
<212> TYPE: DNA
<213> ORGANISM: Artificial Sequence
<220> FEATURE:
<223> OTHER INFORMATION: Fishing probe WSV f460

<400> SEQUENCE: 3
cccacgattc tgatgtgctg gtgaaatgga acctgatggt tggacatcat aaaaacgtgt    60
gtcgtcttac tggtacacaa tttaaggact ctgaaacgtt cttaaagatt ggccatgtca   120
agttctttag gtgcatgaac agtaattctt cgggtgaaaa tcaagcaaac gagttgggtg   180
gttttgcagc taaagaaga acaaagccaa atacgatata taatttggca gaatcgccgc    240
tcatgctttc acctgaaagt acactattga ttatgctaac taaggatca gactacaata    300 gtgcaattgt tagtaactgt gagtacgaca catgggtaag gaaagaagtt gcagtatttg   360
aaaacacgta ctgtacttgt gtgggcggat gggagatttt tttgagtgaa caagaagcta   420
ggaagaataa taaagactgt gatgatagtg ttggtaatat ttctagaaaa aaaaa        475

<210> SEQ ID NO 4
<211> LENGTH: 20
<212> TYPE: DNA
<213> ORGANISM: Artificial Sequence
<220> FEATURE:
<223> OTHER INFORMATION: forward primer Hpv20L

<400> SEQUENCE: 4
tcagcaacag cagacaatcc                                        20

<210> SEQ ID NO 5
<211> LENGTH: 30
<212> TYPE: DNA
<213> ORGANISM: Artificial Sequence
<220> FEATURE:
<223> OTHER INFORMATION: reverse primer Hpv30R
<220> FEATURE:
<221> NAME/KEY: misc_feature
<222> LOCATION: (1)

<223> OTHER INFORMATION: phosphorylated

<400> SEQUENCE: 5
atcctgtatt cttgaccgtt actgtgattt                                30

<210> SEQ ID NO 6
<211> LENGTH: 386
<212> TYPE: DNA
<213> ORGANISM: Artificial Sequence
<220> FEATURE:
<223> OTHER INFORMATION: Fishing probe hpv f390

<400> SEQUENCE: 6
atcctgtatt cttgaccgtt actgtgattt gctaccttta ttttctcctc tccctttgga    60
tctggataat atatgtgtcc cagtaactta ccaaactgta ctggagcact tgtgtatccc   120
actatggttt ctccttgcat ttgtggaatc atttcaaatg cttgcaagtg gttcatctta   180
cctcttgtag ctataatagc ccaactgtcc tcgctctttg ccatgttgtc aatacccccat  240 gcgtttatgt agttactcaa cgcaagattt ccaagtccaa tacttccatg cagtagagcg   300
ttaaaactgt acttaatatc tccactgtta ctgctttcat tcaatcccat cagtcttcgt   360
acaaatggat tgtctgctgt tgctga                                       386

<210> SEQ ID NO 7
<211> LENGTH: 20
<212> TYPE: DNA
<213> ORGANISM: Artificial Sequence
<220> FEATURE:
<223> OTHER INFORMATION: forward primer WS5Mid

<400> SEQUENCE: 7
ttcatcgttg gtgtgttgct                                              20

<210> SEQ ID NO 8
<211> LENGTH: 24
<212> TYPE: DNA
<213> ORGANISM: Artificial Sequence
<220> FEATURE:
<223> OTHER INFORMATION: reverse primer WSSV5

<400> SEQUENCE: 8
cgaagcagag gatgatatcg tacg                                         24

<210> SEQ ID NO 9
<211> LENGTH: 190
<212> TYPE: DNA
<213> ORGANISM: Artificial Sequence
<220> FEATURE:
<223> OTHER INFORMATION: Reporter probe WSV p190

<400> SEQUENCE: 9
ttcatcgttg gtgtgttgct tcaaaacatt caataaatct tcccacctct tggattcttt    60
tctgttacca gacatattat aagaatcgta ctccaatatc ttcctctttt ctagtaggga   120
gaagtgtttc ccaggagtct ccagattcaa aaggcatgat gttaaacgta cgatatcatc   180
ctctgcttcg                                                         190

<210> SEQ ID NO 10
<211> LENGTH: 20
<212> TYPE: DNA
<213> ORGANISM: Artificial Sequence
<220> FEATURE:
<223> OTHER INFORMATION: forward primer Hpvp2L -continued

<400> SEQUENCE: 10
aaggtcacag cagaccaaca                                              20

<210> SEQ ID NO 11
<211> LENGTH: 20
<212> TYPE: DNA
<213> ORGANISM: Artificial Sequence
<220> FEATURE:
<223> OTHER INFORMATION: reverse primer Hpvp2R

<400> SEQUENCE: 11
cataccgttc acgcttttga                                              20

<210> SEQ ID NO 12
<211> LENGTH: 321
<212> TYPE: DNA
<213> ORGANISM: Artificial Sequence
<220> FEATURE:
<223> OTHER INFORMATION: Reporter probe hpv p320

<400> SEQUENCE: 12
aaggtcacag cagaccaaca tcacgtattc atgtttacag acttgagaga tgcaccaatg    60
ataagtgaag taacagcata cctaaacacg gacaatccag cacaaataaa tggcatagga   120
atagagcacc aaggattcga catgtcaaac gatgctaata cagctctcat tggagtcatg   180
ccaagtaact gtataagaaa gaggaaagaa atacagtcag gtatggataa tgtagtactc   240
tggtcaatgc aaagcaatag actgatagac aagagattct ggacaccaga aggttggagt   300
ctcaaaagcg tgaacggtat g                                            321

<210> SEQ ID NO 13
<211> LENGTH: 20
<212> TYPE: DNA
<213> ORGANISM: Artificial Sequence
<220> FEATURE:
<223> OTHER INFORMATION: forward primer TMV-415F

<400> SEQUENCE: 13
caagctcgaa ctgtcgttca                                              20

<210> SEQ ID NO 14
<211> LENGTH: 26
<212> TYPE: DNA
<213> ORGANISM: Artificial Sequence
<220> FEATURE:
<223> OTHER INFORMATION: reverse primer TMV-415RP
<220> FEATURE:
<221> NAME/KEY: misc_feature
<222> LOCATION: (1)
<223> OTHER INFORMATION: phosphorylated

<400> SEQUENCE: 14
accacgtgtg attacggaca caatcc                                       26

<210> SEQ ID NO 15
<211> LENGTH: 415
<212> TYPE: DNA
<213> ORGANISM: Artificial Sequence
<220> FEATURE:
<223> OTHER INFORMATION: TMV fishing probe

<400> SEQUENCE: 15
caagctcgaa ctgtcgttca aagacaattc agtgaggtgt ggaaaccttc accacaagta    60
actgttaggt tccctgacag tgactttaag gtgtacaggt acaatgcggt attagacccg   120

```
ctagtcacag cactgttagg tgcattcgac actagaaata gaataataga agttgaaaat    180
caggcgaacc ccacgactgc cgaaacgtta gatgctactc gtagagtaga cgacgcaacg    240
gtggccataa ggagcgcgat aaataattta atagtagaat tgatcagagg aaccggatct    300
tataatcgga gctctttcga gagctcttct ggtttggttt ggacctctgg tcctgcaact    360
tgaggtagtc aagatgcata taaataacg gattgtgtcc gtaatcacac gtggt          415

<210> SEQ ID NO 16
<211> LENGTH: 20
<212> TYPE: DNA
<213> ORGANISM: Artificial Sequence
<220> FEATURE:
<223> OTHER INFORMATION: forward primer BCTV-4L

<400> SEQUENCE: 16
tgatatgttg ggtgctggtg                                                20

<210> SEQ ID NO 17
<211> LENGTH: 23
<212> TYPE: DNA
<213> ORGANISM: Artificial Sequence
<220> FEATURE:
<223> OTHER INFORMATION: reverse primer BCTV-4RP
<220> FEATURE:
<221> NAME/KEY: misc_feature
<222> LOCATION: (1)
<223> OTHER INFORMATION: phosphorylated

<400> SEQUENCE: 17
ggcatagcct gaccgttatc ggg                                            23

<210> SEQ ID NO 18
<211> LENGTH: 288
<212> TYPE: DNA
<213> ORGANISM: Artificial Sequence
<220> FEATURE:
<223> OTHER INFORMATION: BCTV fishing probe

<400> SEQUENCE: 18
tgatatgttg ggtgctggtg gtataggatc taccattagt aataatggta tgattactat    60
gttgaataat tatgtccagg gtattggtga tagtcagaga gcgaagaacg ttactgtgac   120
gaagcatttg aagtttgata tggctcttat ggggagttct cagttctggg agactcctaa   180
ttatatgacc caatatcatt ggattatcat agacaaggat gttgggtcag tgtttcctac   240
taagttatcg agtatatttg atattcccga taacggtcag gctatgcc                288

<210> SEQ ID NO 19
<211> LENGTH: 20
<212> TYPE: DNA
<213> ORGANISM: Artificial Sequence
<220> FEATURE:
<223> OTHER INFORMATION: forward primer TMV-NF

<400> SEQUENCE: 19
tctgtttagc cggtttgctc                                                20

<210> SEQ ID NO 20
<211> LENGTH: 20
<212> TYPE: DNA
<213> ORGANISM: Artificial Sequence
<220> FEATURE:
<223> OTHER INFORMATION: reverse primer TMV-NR

<400> SEQUENCE: 20
```
aaacccgctg acatcttcac                                          20

<210> SEQ ID NO 21
<211> LENGTH: 256
<212> TYPE: DNA
<213> ORGANISM: Artificial Sequence
<220> FEATURE:
<223> OTHER INFORMATION: TMV reporter probe 1

<400> SEQUENCE: 21
tctgtttagc cggtttggtc gtcacgggcg agtggaactt gcctgacaat tgcagaggag    60
gtgtgagcgt gtgtctggtg gacaaaagga tggaaagagc cgacgaggcc actctcggat   120
cttactacac agcagctgca aagaaaagat ttcagttcaa ggtcgttccc aattatgcta   180
taaccaccca ggacgcgatg aaaaacgtct ggcaagtttt agttaatatt agaaatgtga   240
agatgtcagc gggttt                                                  256

<210> SEQ ID NO 22
<211> LENGTH: 20
<212> TYPE: DNA
<213> ORGANISM: Artificial Sequence
<220> FEATURE:
<223> OTHER INFORMATION: forward primer TMV-2F173

<400> SEQUENCE: 22
ggtcagtgcc gaacaagaac                                          20

<210> SEQ ID NO 23
<211> LENGTH: 20
<212> TYPE: DNA
<213> ORGANISM: Artificial Sequence
<220> FEATURE:
<223> OTHER INFORMATION: reverse primer TMV-173R

<400> SEQUENCE: 23
cacgctgatg acaagaacac                                          20

<210> SEQ ID NO 24
<211> LENGTH: 174
<212> TYPE: DNA
<213> ORGANISM: Artificial Sequence
<220> FEATURE:
<223> OTHER INFORMATION: TMV reporter probe 2

<400> SEQUENCE: 24
ggtcagtgcc gaacaagaac tatagaaatg ttaaggattt tggaggaatg agttttaaaa    60
agaataattt aatcgatgat gattcggagg ctactgtcgc cgaatcggat tcgttttaaa   120
tatgtcttac agtatcacta ctccatctca gttcgtgttc ttgtcatcag cgtg         174

<210> SEQ ID NO 25
<211> LENGTH: 20
<212> TYPE: DNA
<213> ORGANISM: Artificial Sequence
<220> FEATURE:
<223> OTHER INFORMATION: forward primer BCTV-RF

<400> SEQUENCE: 25
gtgcgcaatt tgaacatgag                                          20

<210> SEQ ID NO 26
<211> LENGTH: 21
<212> TYPE: DNA
<213> ORGANISM: Artificial Sequence
<220> FEATURE:

<223> OTHER INFORMATION: reverse primer BCTV-RR

<400> SEQUENCE: 26
cagaaccaga gtgttgcaat g                                              21

<210> SEQ ID NO 27
<211> LENGTH: 219
<212> TYPE: DNA
<213> ORGANISM: Artificial Sequence
<220> FEATURE:
<223> OTHER INFORMATION: BCTV reporter probe

<400> SEQUENCE: 27
gtgcgcaatt tgaacatgag gactatttgg aaagacaccg gtggtgggaa gtatgaagac    60
gtgaaggaga atgctttact ctatgttgtt gttaatgata tacggataa tactaatatg   120 tatgccacat tatttggcaa ttgtagatgc tatttttatt aataatattt attattaata   180
atgaaattag tacaagttca ttgcaacact ctggttctg                          219

<210> SEQ ID NO 28
<211> LENGTH: 25
<212> TYPE: DNA
<213> ORGANISM: Artificial Sequence
<220> FEATURE:
<223> OTHER INFORMATION: forward primer MCP 408F

<400> SEQUENCE: 28
ctacgctgta ctgacaagtg aggag                                          25

<210> SEQ ID NO 29
<211> LENGTH: 29
<212> TYPE: DNA
<213> ORGANISM: Artificial Sequence
<220> FEATURE:
<223> OTHER INFORMATION: reverse primer MCP 408RP
<220> FEATURE:
<221> NAME/KEY: misc_feature
<222> LOCATION: (1)
<223> OTHER INFORMATION: phosphorylated

<400> SEQUENCE: 29
gtataacagt aggtcataac accatccat                                      29

<210> SEQ ID NO 30
<211> LENGTH: 408
<212> TYPE: DNA
<213> ORGANISM: Artificial Sequence
<220> FEATURE:
<223> OTHER INFORMATION: MCP fishing probe

<400> SEQUENCE: 30
ctacgctgta ctgacaagtg aggagcgtga ggttgtggcc cagtctagcc gtagcatgct    60
cattgagcag tgtcaggtgg cgcctcgtgt gcctgtcaca cccgtagaca attccttggt   120
gcatctcgac ctgaggttca gtcaccctgt gaaggccttg ttctttgcag tcaagaatgt   180
cactcaccgc aacgtgcaaa gcaattacac cgcggccagc cccgtgtatg tcaacaacaa   240
ggtgaatctg cctttgctgg ccaccaatcc cctgtccgag gtgtcgctca tttacgagaa   300
cacccctcgg ctccaccaga tgggagtaga ctgcttcaca tctgtcgacc cctactactt   360
tgcgcccagc atgcctgaga tggatggtgt tatgacctac tgttatac                408

<210> SEQ ID NO 31
<211> LENGTH: 20
<212> TYPE: DNA

```
<213> ORGANISM: Artificial Sequence
<220> FEATURE:
<223> OTHER INFORMATION: forward primer MCP 282F

<400> SEQUENCE: 31
gggtggcgac tacctcatta                                               20

<210> SEQ ID NO 32
<211> LENGTH: 20
<212> TYPE: DNA
<213> ORGANISM: Artificial Sequence
<220> FEATURE:
<223> OTHER INFORMATION: reverse primer MCP 282R

<400> SEQUENCE: 32
ggcatagtct gaccgttggt                                               20

<210> SEQ ID NO 33
<211> LENGTH: 282
<212> TYPE: DNA
<213> ORGANISM: Artificial Sequence
<220> FEATURE:
<223> OTHER INFORMATION: MCP reporter probe

<400> SEQUENCE: 33
gggtggcgac tacctcatta atgtgtggct gcgtgttaag atcccctcca tcacgtccag    60
caaggagaac agctacattc gctggtgtga taatttgatg cacaatctag ttgaggaggt   120
gtcggtgtca tttaacgacc tggtggcaca gaccctgacc agcgagttcc ttgacttttg   180
gaacgcctgc atgatgcctg gcagcaaaca atctggctac aacaagatga ttggcatgcg   240
cagcgacctg gtgggcggta tcaccaacgg tcagactatg cc                     282

<210> SEQ ID NO 34
<211> LENGTH: 20
<212> TYPE: DNA
<213> ORGANISM: Artificial Sequence
<220> FEATURE:
<223> OTHER INFORMATION: forward primer Pem-5

<400> SEQUENCE: 34
ctatccttca ggtcttgcac                                               20

<210> SEQ ID NO 35
<211> LENGTH: 20
<212> TYPE: DNA
<213> ORGANISM: Artificial Sequence
<220> FEATURE:
<223> OTHER INFORMATION: reverse primer Pem300RP
<220> FEATURE:
<221> NAME/KEY: misc_feature
<222> LOCATION: (1)
<223> OTHER INFORMATION: phosphorylated

<400> SEQUENCE: 35
ggcgatgtta acgaaagctc                                               20

<210> SEQ ID NO 36
<211> LENGTH: 285
<212> TYPE: DNA
<213> ORGANISM: Artificial Sequence
<220> FEATURE:
<223> OTHER INFORMATION: (CHH/GIH/MIH) fishing probe

<400> SEQUENCE: 36
ctatccttca ggtcttgcac gggcgcctac gaccgcgaac tccttgtaag gctcgaccgc    60
```

```
gtgtgcgaag actgctacaa cgtgtaccgc gacgtcggag tggcagccga atgcaggtaa        120
cttattactt tgcagtaacc cacccagttg tgttgtgatt aaagactatt gtagaagcgt        180
attagtatac catctattac tttagtatat catctattac tatcatctat cggacaatga        240
tttcatactg agtttgttat ccatggagct ttcgttaaca tcgcc                       285
```

```
<210> SEQ ID NO 37
<211> LENGTH: 20
<212> TYPE: DNA
<213> ORGANISM: Artificial Sequence
<220> FEATURE:
<223> OTHER INFORMATION: forward primer Pem-CL

<400> SEQUENCE: 37
agagcctgga agttgctgac                                                    20

<210> SEQ ID NO 38
<211> LENGTH: 19
<212> TYPE: DNA
<213> ORGANISM: Artificial Sequence
<220> FEATURE:
<223> OTHER INFORMATION: reverse primer Pem-2R165b

<400> SEQUENCE: 38
aagaacggag gaacgttgg                                                     19

<210> SEQ ID NO 39
<211> LENGTH: 167
<212> TYPE: DNA
<213> ORGANISM: Artificial Sequence
<220> FEATURE:
<223> OTHER INFORMATION: (CHH/GIH/MIH) reporter probe 1

<400> SEQUENCE: 39
agagcctgga agttgctgac cgtcgctccc gatctgcctc tactctaaag atatggttgc        60
cgttggaccg atgcgggcag ctgtcctggt gtccctgctg ttggcaatcc cggcctctgc       120
caccaccttc ggagacggaa atgacattcc aacgttcctc cgttctt                    167

<210> SEQ ID NO 40
<211> LENGTH: 22
<212> TYPE: DNA
<213> ORGANISM: Artificial Sequence
<220> FEATURE:
<223> OTHER INFORMATION: forward primer Pem-R602F

<400> SEQUENCE: 40
ttcacatttc tcctgtacga cc                                                 22

<210> SEQ ID NO 41
<211> LENGTH: 20
<212> TYPE: DNA
<213> ORGANISM: Artificial Sequence
<220> FEATURE:
<223> OTHER INFORMATION: reverse primer Pem-3

<400> SEQUENCE: 41
gtactggttc ctttgacgag                                                    20

<210> SEQ ID NO 42
<211> LENGTH: 135
<212> TYPE: DNA
<213> ORGANISM: Artificial Sequence
<220> FEATURE:
<223> OTHER INFORMATION: (CHH/GIH/MIH) reporter probe 2
```

```
<400> SEQUENCE: 42
ttcacatttc tcctgtacga cctaccagtg gaactacata acattattcc ttccttcagg      60
agtaactgtt tccacaacga ggtgttcctc tactgtgtgg actacatgtt ccggcctcgt    120
caaaggaacc agtac                                                      135

<210> SEQ ID NO 43
<211> LENGTH: 30
<212> TYPE: DNA
<213> ORGANISM: Artificial Sequence
<220> FEATURE:
<223> OTHER INFORMATION: forward primer Vvh383F

<400> SEQUENCE: 43
ctaaacagta atgatgtgtt gtatgtcaat                                       30

<210> SEQ ID NO 44
<211> LENGTH: 30
<212> TYPE: DNA
<213> ORGANISM: Artificial Sequence
<220> FEATURE:
<223> OTHER INFORMATION: reverse primer Vvh383RP
<220> FEATURE:
<221> NAME/KEY: misc_feature
<222> LOCATION: (1)
<223> OTHER INFORMATION: phosphorylated

<400> SEQUENCE: 44
gtaaaagaga aagggtaaac agagtcattt                                       30

<210> SEQ ID NO 45
<211> LENGTH: 383
<212> TYPE: DNA
<213> ORGANISM: Artificial Sequence
<220> FEATURE:
<223> OTHER INFORMATION: cytolysin fishing probe

<400> SEQUENCE: 45
ctaaacagta atgatgtgtt gtatgtcaat gtaggaacag caaccgatga cgaaatcact      60
caagcaaaaa gtcatatcat ctccggtagc accgtggtga ttgatttgac tcaaattgct    120
ggtgacgacg caaggcttga ttggagccaa aaactcactg gtttaggact gtcagcgcct    180
gttgtggtta cggggggttta tcaaggcgac gccttagtca atgcgattgt cagcgatgtc    240
accgacgaga atgacaaccc aatcaacgat ccccaagccg agttagagag cgttaaactt    300
tctctcactc atgccctaga ccgcttccaa tctgagggaa ataagatga aaaaaatgac    360 tctgtttacc ctttctcttt tac                                            383

<210> SEQ ID NO 46
<211> LENGTH: 20
<212> TYPE: DNA
<213> ORGANISM: Artificial Sequence
<220> FEATURE:
<223> OTHER INFORMATION: forward primer Vvh266F

<400> SEQUENCE: 46
aggtgcggaa gtgaacaaag                                                  20

<210> SEQ ID NO 47
<211> LENGTH: 20
<212> TYPE: DNA
<213> ORGANISM: Artificial Sequence
<220> FEATURE:
<223> OTHER INFORMATION: reverse primer Vvh428R
```

```
<400> SEQUENCE: 47
atcaaatacc cagccactgc                                                20

<210> SEQ ID NO 48
<211> LENGTH: 241
<212> TYPE: DNA
<213> ORGANISM: Artificial Sequence
<220> FEATURE:
<223> OTHER INFORMATION: cytolysin reporter probe

<400> SEQUENCE: 48
aggtgcggaa gtgaacaaag acggcccgaa agtgggtggc gaagtcagtg gctcatttac      60
ctacaactac tcgaagacct tggtgtttga tacaaaagac tatcgcatca acaaccgttc     120
atcattgagt gattttgata tttcattcga gcgtgaattt ggggaatgtg atgaactgcg     180
ccgccaagag cttggatgct atttcaccgc cgctcactgg ggcagtggct gggtatttga     240
t                                                                     241
```

KIT AND METHOD FOR QUANTITATIVELY DETECTING MULTIPLE PATHOGENIC MICROORGANISMS WITHOUT GENE AMPLIFICATION

TECHNICAL FIELD

The present invention relates to a kit and method for quantitatively detecting multiple pathogens without a gene amplification which are able to accurately quantitatively detect multiple pathogens in a combination with a hybridization reaction and an enzyme-linked immune system method without a purification and amplification of a gene material.

BACKGROUND ART

Generally, a diagnosis method of multiple pathogens is classified into a immune method for detecting a certain antibody of multiple pathogens, and a method for amplifying a specific gene using a PCR. Estimating an organism, which is a cause of a disease based on a symptom observation, is a traditional method, but it is not a direct diagnosis method. So, it is needed to confirm multiple pathogens of a disease by observing a microorganism of multiple pathogens using a microscope or using an immune reaction with respect to an antibody. However, when a microscope method is adapted, the multiple pathogens should be large enough to be observed by a microscope, and the density of the same should be high so that it can be easily searched from a sample. The type of the same should be clearly classified from other organisms. Namely, in case of a small organism such as virus and bacteria having similar shapes, it is impossible to impossible to accurately diagnose using a microscope.

The immune method for tracing an antibody of multiple pathogenic microorganisms is able to accurately diagnose a reason organism, but the density of the reason organism should be enough high, and it is impossible to obtain an antibody all the time with respect to a unique antibody of all reason organisms.

The most advanced technology for diagnosing multiple pathogenic microorganisms is a PCR method for amplifying a certain gene of multiple pathogens, and for conforming and diagnosing the presence of the gene. Since the PCR method is directed to amplifying a certain gene using a DNA or RNA gene that all organism commonly have, when there is information on a certain gene, it is possible to diagnose all organisms irrespective of the size, type and density of an organism. An accurate ration of multiple pathogens may be possible using a recently developed real-time PCR method.

The PCR method may have a very accurate and precious diagnosis, but since it needs a gene amplification process, various factors may affect the same. For example, impurities remaining after purifying the gene substances may retard the amplification or a specific amplification may be performed. Much time and cost need during a purification of gene substances and an amplification of gene. An expensive precious machine and a skilled expert are further needed.

DISCLOSURE OF INVENTION

Accordingly, it is an object of the present invention to develop and provide a kit for quantitatively detecting an organism which is a cause of a disease by directly testing a specific organism gene based on a combination of a hybridization reaction and an enzyme-linked immunosorbentassay (ELISA) without a gene amplification after an intensive research and effort.

It is another object of the present invention to provide a kit and method for accurately and quantitatively detecting multiple pathogens using a hybridization reaction and ELISA with a lower cost.

ADVANTAGEOUS EFFECTS

As described above, a multiple quantitative detection kit of a specific multiple pathogenic microorganisms is able to accurately and simply diagnose multiple pathogenic microorganisms using a hybridization reaction and an enzyme immune analysis method without a purification or amplification of a specific gene of a multiple pathogenic microorganisms and is able to be adapted to all kinds of organisms including virus, bacteria and single cell microorganism. Various kinds of multiple pathogenic microorganisms can be concurrently diagnosed and can be repeatedly performed, so that it is very useful to a quantitative detection of multiple pathogenic microorganisms.

BRIEF DESCRIPTION OF THE DRAWINGS

The present invention will become better understood with reference to the accompanying drawings which are given only by way of illustration and thus are not limitative of the present invention, wherein;

FIG. 1 is a view illustrating a process that a DNA hybridization module fixed with a fishing probe according to the present invention;

FIG. 2 is a view illustrating a process that multiple pathogens are detected based on a hybridization reaction and ELISA using a DNA hybridization module of FIG. 1;

FIG. 3 is a view illustrating a portion that a fishing prove and reporter probe recognize in a genome base sequence of a white spot virus (WSSV) and a primer designed for amplifying the same according to the present invention;

FIG. 4 is a view illustrating a portion that a fishing probe and a reporter probe recognize in a genome base sequence of a hepatopancreatic parvo-like virus (Hpv) and a primer designed for amplifying the same according to the present invention;

FIG. 5 is a view illustrating an arrangement for multiply analyzing concurrently various multiple pathogens based on a DNA hybridization module of FIG. 1, of which A is an arrangement for detecting 2 kinds of multiple pathogens; and B is an arrangement for detecting 12 kinds of multiple pathogens; and FIG. 6 is a view illustrating an arrangement for quantitatively analyzing multiple pathogens based on a DNA hybridization module of FIG. 1;

FIGS. 7 and 8 are views of standard curves made with Hpv and WSSV using a detection kit according to the present invention;

FIGS. 9 and 10 are views of results of a detection of Hpv and WSSV with respect to an actual sample using a regression curve of a standard curve made based on a detection kit according to the present invention;

FIGS. 11 and 12 are views of a standard curve made with a standard sample of tobacco mosaic virus (TMV) and beet curly top virus (BCTV) using a detection kit and are views of a result of a detection of TMV and BCTV with respect to an actual sample using the same;

FIGS. 13 and 14 are views of a standard curve made with a standard sample of a rock bream iridovirus (RBIV)-linked MCP gene using a detection kit and a result of a RBIV-linked MCP gene with an actual sample using the same;

FIGS. 15 and 16 are views of a standard curve made with a standard sample of a penaeus chinensis-linked CHH/GIG/MIH gene using a detection kit and a result of a penaeus chinensis-linked CHH/GIH/MIH with an actual sample using the same; and FIGS. 17 and 18 are views of a standard curve made with a standard sample of a vibro vulnificus-linked cytolysin gene using a detection kit and a result of a detection of a vibro vulnificus-linked cytolysin gene with an actual sample according to the present invention.

BEST MODE FOR CARRYING OUT THE INVENTION

To achieve the above objects, there is provided a kit for quantitatively and accurately diagnosing multiple pathogens in a combination with a hybridization reaction and an ELISA without a purification or amplification of a gene substance while including a fishing-fixed hybridization module, a tag-labeled reporter probe, a standard sample, a hybridization buffering solution, a denature solution, a neutralization solution, an antibody dilution solution, an enzyme-linked anti-tag antibody, and a substrate solution of the above enzyme.

In addition, the present invention provides a method for quantitatively detecting multiple pathogens using the kit of the present invention.

The present invention will be described in detail with reference to the accompanying drawings. in the description of the present invention, the term "fishing probe" means a polynucleotide (or single strand DNA chain) having a base sequence for recognizing a specific gene portion of multiple pathogens to be detected and forms a triple composite of a fishing probe-analysis sample-reporter probe with a hybridization with an analysis sample and reporter probe including a specific gene portion.

The term "reporter probe" means a tag-labeled double stand polynucleotide (or double strand DNA chain) having a base sequence for recognizing a specific gene portion not overlapped with a recognition portion of a fishing probe in the specific genes of multiple pathogens to be detected and forms a triple composite of a fishing probe-analysis sample-reporter probe with a hybridization with an analysis sample and fishing probe.

The term "standard sample" means a PCR-amplified DNA which includes the specific gene portions recognized by the fishing probe with a main type of the gene of the multiple pathogens to be detected and all specific gene portions which are recognized by means of the reporter probe.

The kit for quantitatively detecting the multiple pathogens according to the present invention comprises:

1) a hybridization module fixed with a fishing probe;
2) a reporter probe labeled with a tag;
3) a standard sample;
4) a hybridization buffer solution;
5) a washing solution;
6) a denature solution;
7) a neutralization solution;
8) an antibody dilution solution;
9) an enzyme-linked anti-tag antibody; and
10) a substrate solution of the above enzyme.

The hybridization module fixed with a fishing probe comprises:

1) a step in which a pair of fishing primers for amplifying a fishing probe is prepared for recognizing a specific gene portion of multiple pathogens, and a reverse direction fishing primer is covalent-bonded at a surface of an analysis container among the above primers;

2) a step in which a fishing probe is amplified based on a solid phase PCR reaction using the pair of the fishing primers;

3) a step in which only the fixed single strand fishing probe is remained by denaturing the DNA, and the remaining strands are removed; and 4) a step in which a non-specific binding capacity of the surface of the container is removed using a non-specific DNA (refer to FIG. 1).

In the step 1, the fishing probe is a single strand polynucleotide including a specific gene portion of multiple pathogens and is amplified based on a solid phase PCR reaction using a pair of the fishing primers designed for recognizing the gene portions.

So as to covalent-bonding a fishing primer oh the solid surface of the analysis container, it is needed to prepare a Nuclelink™ strip module, NUNC Inc. of which an operation radical is exposed for forming a covalent bonding with an end of phosphorylation of a primer on a surface and a 5'-phosphorylated primer are needed.

At this time, all 5'-end of bi-directional primers are not phosphorylated, but only 5'-end of reverse direction primer is phosphorylated and is fixed at the module. A normal direction primer is added to a PCR reaction solution and is provided in a liquid phase. So, a hybridization reaction and denature with respect to the main type may freely occur in the normal direction primer, and it is possible to increase an annealing efficiency during the PCR reaction.

The reverse direction fishing primer of 100 through 200 ng (about 10 through 20 pmol) per each reaction well is diluted in 10 M 1-methyl-imidazole solution of 80 ul and 1-ethyl-3-(3-dimethylaminopropyl)-carbodiimide solution, and a mixture is added to a micro cup of the module with the same volume and is reacted for 1 through 3 days at 50° C. As the reaction time passes, the reaction solution is discarded, and a NaOH denature solution (Tween 20 contained) of 1.1 through 2 times volume of the reaction liquid is added, and it is washed three times for 2 minutes at 50° C. and one time for 125 minutes and three times for 2 minutes, respectively. A neutralization solution is added to the washed container by the same volume as the denature liquid, and it is washed three times for 15 minutes.

In the step 2, a fishing primer is extended from the reverse direction fishing primer fixed on the surface of the analysis container in the step 1. A solid phase PCR reaction solution of 50 ul containing a normal direction and reverse direction fishing primer is inputted into each small cup of the modules, and the PCR reaction is performed.

When the PCR is finished in the step 2, the reaction solution is discarded, and NaOH denature solution (containing tween 20) of 1.5 times or 2 times volume is added, and it is washed at 50 through 55° C. three times for 2 minutes, 1 time for 15 minutes, and 3 times for 15 minutes, and only a fixed single strand fishing probe is remained, and the remaining strands are removed. A neutralization solution (100 mM Tris-HCl (pH 7.5), 150 mM NaCl, 0.1% Tween 20) of the same volume is added and washed three times for 15 minutes, and the remaining NaOH denature solution is removed.

In the fourth step, a non-specific DNA solution is added by the same amount as the hybridization buffer solution of 50 ul in each small cup of the modules, and the hybridization buffer solution is discarded, and NaOH denature solution (Tween 20 contained) of 1.5 through 2 times volume is added, and is washed at 50 through 55° C. 3 times for 2 minutes, 1 time for 15 minutes, and 3 times for 2 minutes, so that a non-specific attaching force of the surface of the analysis container is removed.

The thusly prepared module is sealed and stored at 4° C.,
The tag-labeled reporter probe is manufactured as follows.

First, a specific gene portion not overlapped with a specific gene portion recognizable by a fishing probe is selected in the multiple pathogens, and a pair of primers are prepared for amplifying the above portion.

The PCR is performed using a pair of the primers with respect to the genome DNA of the multiple pathogens, and a reporter probe DNA piece is amplified. At this time, dUTP labeled with the tag along with the dNTP, for example, a dUTP labeled with digoxygenin, biotin, fluorescein, etc. may be added or a deoxynucleotide labeled with a radioactive isotope may be added for thereby performing a PCR reaction, so that it is possible to amplify a reporter probe labeled with the tag. The amplified material is purified with an agarose gel, and the concentration is measured and is stored at 4° C.

The standard sample is prepared by amplifying a specific gene of multiple pathogens using the PCR. The portion recognizable by the fishing probe and the portion recognizable by the reporter probe may be all included. The amplified standard sample is purified in an agarose gel, and the amount of the DNA is quantified, and the mol concentration is measured, and the gene copy number is computed.

The hybridization buffer solution for forming a triple composite formed of a fishing probe-analysis sample-reporter probe consists of 10×SSC (1.5M NaCl, 0.15M sodium citrate, pH 7.0). 0.2% of sarcosine, 0.04% SDS (Sodium docecyl sulfate), 0.2% of blocking solution (0.2% skim milk protein (w/v) 50 mM, Tris-HCl 150 mM, pH 7.4) and 1 through 4 mM CTAB (cetyltrimethylmmonium bromide).

The washing solution consists of 0.5× through 2×SSC (75 through 300 mM NaCl, 7.5 through 30 mM sodium citrate, pH 7.0) solution. In the washing step after a preliminary hybridization reaction, 0.5×SSC (75 mM NaCl, 7.5 mM sodium citrate, pH 7.0) solution is used, and in the washing step for removing a reporter probe which is bonded with a hybridization buffer solution remaining after the hybridization reaction, 2×SSC (300 mM NaCl, 30 mM sodium citrate, pH 7.0); 1×SSC (150 mM NaCl, 15 mM sodium citrate, pH 7); and 0.5×SSC (75 mM NaCl sodium citrate, pH 7.0) are sequentially used.

As the denature solution, 0.4N NaOH (0.25% Tween 20 contained) solution and 0.2N NaOH (0.1% Tween 20 contained) solution are used. 0.4N NaOH (0.25% Tween 20 contained) solution is used for removing a fishing primer which is not covalent-bonded on the surface of the analysis container during a hybridization module manufacture fixed with the fishing probe.

In addition, the solution of 0.2N NaOH (0.1% Tween 20 contained) is used for removing the remaining strands except the fishing probe of a single strand fixed on the surface of the analysis container, and for removing a non-specific DNA used for removing a non-specific attaching force, and for removing an analysis sample and a reporter probe hybridized at the fishing probe of the analysis container after the analysis is completed for thereby recycling the analysis container.

The neutralization solution is used for neutralizing the same after the denature solution and activating a fishing probe attached to the analysis container and contains 100 mM Tris-HCl (pH 7.5), 150 mM NaCl and 0.1% Tween 20.

The antigen dilution solution is used for diluting an enzyme-linked anti-tag antibody to be used for an ELISA analysis with a certain concentration and contains 1% defatted protein (w/v), 50 mM Tris-HCl (pH 7.4) and 150 mM NaCl.

Here, the enzyme-linked anti-tag antibody is an antibody with respect to the tag labeled with a reporter probe and is linked with an enzyme which may cause a coloring reaction by way of a reaction with a base. For the above enzyme, horseradish peroxidase, alkaline phosphatase, and .beta.-galactosidase may be used.

The enzyme-linked anti-tag antibody is linked with a tag labeled on a reporter probe in a triple composite consisting of a fishing probe-analysis sample-reporter probe and has a generation reaction by way of a reaction of the added base. So, it is possible to quantitatively confirm whether the analysis sample is infected by corresponding multiple pathogens to be detected. At this time, as the base of the enzyme, the base proper to an enzyme of luminol, 4-nitrophenyl phosphate, CSPD (Disodium 3-(4-methoxyspiro 1,2-dioxetane-3,2-(5-chloro) tricycle [3.3.1.13,7]decan-4-yl)phenyl phosphate), X-gal (5-bromo-4-chloro-3-indolyl-beta-d-galactoside), etc. may be used.

In addition, the present invention provided a method for quantitatively detecting multiple pathogens using the kit according to the present invention (refer to FIG. 2).

The above method comprises:

1) a step in which a method for activating a fishing probe fixed at a hybridization module;

2) a step in which an analysis sample, a reporter probe and a hybridization buffer solution are inputted into the hybridization module, and a hybridization reaction is induced, and a triple composite consisting of a fishing probe-analysis-reporter probe is formed;

3) a step in which the amount of the triple composite is measured using an ELISA; and 4) a step in which it is recycled by washing the hybridization module.

In the above step 1, a hybridization module fixed with the fishing probe designed for recognizing a specific gene portion of a corresponding multiple pathogenic microorganisms in accordance with the kind of a multiple pathogenic microorganisms to be analyzed is inserted into a fixing frame in a certain combination, and it is washed three times for 15 minutes with a so neutralization solution (100 mM Tris-Cl (pH 7.5), 150 mMNaCl, 0.1% Tween 20).

In the step 2, it corresponds to a hybridization step for forming a triple composite consisting of a fishing probe-analysis sample-reporter probe. In the above step, an analysis sample and a reporter probe having an labeled tag are mixed, and is denatured for 10 through 20 minutes at 95~100° C., and is added to a hybridization module fixed with a fishing probe along with a hybridization buffer solution by the same amount. The hybridization module is lightly agitated for 1 through 3 hours at 50~55° C., and a hybridization reaction is induced, and a triple composite consisting of a fishing probe-analysis sample-reporter probe is formed.

At this time, the analysis sample is prepared as follows.

An organism sample used for checking an infection of multiple pathogens is chopped or homogenized, and a protein decomposition enzyme K (proteinase K) is treated for 1 through 3 hours at 37 through 50° C. The supernatant obtained a centrifugation process of the reaction solution is added with 100% ethanol of two times volume, and a gene substance is deposited and used as an analysis sample.

When the analysis sample is concentrated, the gene substance is deposited and dissolved with distilled water with the volume less than the volume of the solution before deposit and is used. When it is needed to decrease the manufacturing time of the analysis sample solution, there may be a step in which the ethanol deposit process is omitted, and the supernatant may be directly used. In the step 1 before the hybridization reaction of the step 2, a hybridization buffer solution of the same volume as the distilled water including a 0.3% blocking solution is added to the hybridization module, and a preliminary hybridization reaction is performed. In the preliminary hybridization step, 0.3% blocking solution is additionally added, namely, the totally 0.5% blocking solution is used.

The preliminary hybridization reaction is performed for preventing that a sample DNA or a reporter probe DNA is abnormally attached to a wall of the plastic module. It is preferably performed for 0.5 through 1 hour at 50 through 55° C. In this step, a blocking solution (1% skim milk protein (w/v) 50 mM, Tris-HCl 150 mM, pH 7.4) is used, preferably 0.2% through 0.6% is used, so that it is possible to prevent a nonspecific bonding of the sample DNA or the reporter probe. The hybridization buffer solution used for a preliminary hybridization reaction does not include a DNA, the CTAB is not preferably included.

When the preliminary hybridization is performed, the module that the preliminary hybridization is completed is washed with a washing solution at the same temperature of 50~55° C., and the hybridization reaction is performed. At this time, the washing process is performed using a 0.5×SSC solution (75 mM NaCl, 7.5 mM sodium citrate, pH 7.0). During the hybridization reaction, the hybridization module is slightly swung with 250 through 350 rpm for 2 hours at 55° C. in the container with 100% moisture.

When the hybridization reaction of the step 2 is completed, the hybridization module is washed at 50 through 55° C. before the ELISA analysis of the step 3, and it is preferably to remove a non-reacted substance which does not form a triple composite of a fishing probe-analysis sample-reporter probe. At this time, the washing solution is a 0.5× through 2×SSC (75 through 300 mM NaCl, 7.5 through 30 mM sodium citrate, pH 7.0) solution, and it is washed three times for 2 minutes with a 2×SSC (300 mM NaCl, 30 mM sodium citrate, pH 7.0) solution for fully removing the reporter probe which is not bonded with a hybridization buffer solution remaining after the hybridization reaction, and it is washed one time for 15 minutes with a 1×SSC (150 mM NaCl, 15 mM sodium citrate, pH 7.0) solution, and it is washed three times for 2 minutes with a 0.5×SSC (75 mM NaCl, 7.5 mM sodium citrate, pH 7.0) solution.

The step 3 is an ELISA step in which an antigen-antibody reaction is induced reacting for 1 through 3 hours at 20 through 25° C. by adding an enzyme-linked anti-tag antibody which recognizes a tag of a reporter probe in a triple composite in a module which finished the hybridization reaction. The non-bonded antibody is washed seven times with a neutralization solution, and the base of the enzyme linked with the above antibody is added and reacted at a proper temperature, and a light emitting or color emission reaction is induced.

An enzyme activation is combined by measuring the induced light and color emission degrees using a luminometer or an ELISA reader. At this time, the enzyme activation measured in each analysis sample is compared with a standard curve obtained from the standard sample DNA, and the amount of multiple pathogenic microorganisms is determined.

In the step 4, the reaction solution is discarded after the ELISA analysis, and the hybridization module is recycled for the reuse of the same by removing the analysis sample and reporter probe hybridized to the fishing probe. A 0.2N NaOH denature solution (Tween 20 contained) of 1.5 times volume is added to the hybridization module, and it is washed three times for 3 minutes at 50 through 60° C. and is washed one time for 15 minutes and then is washed for one hour with a 0.1% CTAB solution at the same temperature and is washed for one hour with a 0.2% sarcosine (0.1% SDS and 0.1% Tween 20 contained). At this time, when the measurement value is very high, a washing work of a 0.1% CTAB solution and a 0.1% sarcosine solution may be performed one time or two times for the full washing. In case that a small amount of DNA is hybridized, it is possible to effectively recycle the hybridization module with three times washing for 15 through 30 minutes with a 0.1 N NaOH denature solution (Tween 20 contained). When the measurement value is more than 200000 RLU, the above multi-step washing processes may be preferably performed.

It is possible to check whether the washing is substantially performed or not by measuring an activation after the hybridization by inputting only a reporter prove DNA in a state that the standard DNA is not inputted.

According to an example of the present invention, a fishing probe and a reporter probe (FIGS. 3 and 4) are designed so that WSSV and Hpv can be detected, which may cause a virus related diseases in penaeus chinensis, and a detection kit for using the above same is manufactured. The standard sample DNAs of The WSSV and Hpv are detected using the detection kit, so that it is possible to quantitatively detect the standard sample DNAs of the WSSV and Hpv that are the targets to be detected using the multiple pathogenic microorganisms detection kit of the present invention (refer to FIGS. 7 and 8).

The virus is quantitatively measured using the detection kit of the present invention with respect to the penaeus chinensis infected with the WSSV and Hpv and the penaeus chinensis which is not infected, so that it is possible to specifically detect a corresponding virus using the diagnosis kit of the present invention (refer to FIG. 10).

The detection kit of the present invention is able to detect a BCTV virus of a ss DNA virus and a TMV virus which is a single strand RNA virus (ss RNA virus) within an effective measurement scope (refer to FIGS. 6A and 6B), and it is possible to detect a double strand DNA gene as well as a single strand DNA gene and a single strand RNA gene.

The detection kit of the present invention is able to specifically detect the major capsidprotein (MCP) of the rock bream iridovirus (PBIV) based on the infection steps of the virus along with the kinds of the infected fishes (refer to FIGS. 13 and 14). It is useful for analyzing an infection spread aspect of the virus, and it is possible to specifically detect a CHH/GIH/MIH (Crustachean Hyperglycemic Hormone[CHH]/Gonad Inhibiting Hormone[GIH]/Molt-Inhibiting Hormone[MIH] gene (refer to FIGS. 15 and 16).

The detection method using the hybridization module according to the present invention is capable of detection a virus and bacteria as well as the genes of multi-cell organisms having larger size genes. The detection kit according to the present invention is capable of specifically detecting similar bacteria such as *Vibrio vulnificus* and *Vibrio haemolyticus* (refer to FIGS. 17 and 18).

So as to analyze various kinds of multiple pathogens using the kit of the present invention at the same time, the following module arrays are possible.

Assuming that a hybridization module of 1×8 is arranged at a 96-well microplate type fixing frame (NUNC frame) of 8×12, it is possible to arrange various combinations of hybridization modules fixed with different fishing probes based on the kinds of multiple pathogens to be detected.

For example, when it is needed to detect two kinds of multiple pathogenic microorganisms, each hybridization module fixed with two kinds of fishing probes are arranged alternately at each hybridization module (refer to A of FIG. 5), and when it is needed to detect 12 kinds of multiple pathogenic microorganisms, a hybridization module fixed with different kinds of fishing probes are arranged at each row (refer to B of FIG. 5).

So as to quantitatively analyze the numbers of multiple pathogenic microorganisms, the following module arrangements are possible. For the above quantitative analysis, a standard sample, which knows the number of gene copies of specific genes, is needed. When the samples are arranged, a standard sample (Sta; standard a, STb; standard b) is arranged at the second row B, so that it becomes the standard of the quantitative degree (refer to FIG. 6). When it is needed to draw a standard curve for an accurate diagnosis, the diluted standard samples are arranged from the second row to the eighth row of the standard sample row.

In addition, so as to increase the sensitivity of the method for quantitatively detecting the multiple pathogenic microorganisms using the kit of the present invention, the following method may be adapted.

The gene portions that are recognized by the report probe with respect to the multiple pathogenic microorganisms of one kind are selected in multiple numbers, and a plurality of report probes are hybridized, and a triple composite hybridized with one fishing probe-analysis sample and a plurality of reporter probes is formed, and the strength of the signals finally detected in proportion to the number of the hybridized reporter probes increases. When the analysis sample is deposited and concentrated and used, or the specific gene of the multiple pathogenic microorganisms of the analysis sample is previously amplified with PCR and is used, it is possible to detect the multiple pathogenic microorganisms less than 10 gene copies.

In addition, when the base of the enzyme linked with the antibody is selected, it is possible to significantly increase the sensitivity by using a phosphorus base or a light emitting base instead of using the color emitting base.

So as to increase a specific property with the method for quantitatively detecting the multiple pathogenic microorganisms using the kit of the present invention, the following methods may be considered.

A plurality of gene portions that are recognized by the fishing probe and the reporter probe with respect to one kind of multiple pathogenic microorganisms are selected, and a hybridization reaction is induced using a combination of the different fishing probe and reporter probe designed for recognizing the same, so that it is possible to separate and detect the multiple pathogenic microorganisms having similar genes.

The strength of the final signal may be changed in accordance with the dilution ratio by diluting and analyzing the analysis samples in multiple numbers, and the non-specific reaction does not have a change in proportion to the dilution ratio, so that it is possible to separate a specific reaction.

The embodiments of the present invention will be described in detail.

The following embodiments are provided for illustrative purposes and are not limited to the disclosed contents of the present invention.

Embodiment 1

So as to manufacture a non-amplification multiple quantitative detection kit of multiple pathogenic microorganisms using a hybridization reaction and ELISA of a multiple pathogenic microorganisms detection kit according to the present invention, WSSV and Hpv are selected, which are known to cause a virus disease from penaeus chinensis as multiple pathogenic microorganisms to be detected. Here, the WSSV is a double strand DNA virus, and the Hpv is a single strand DNA virus.

[1-1] Manufacture of Hybridization Module Fixed with Fishing Probe

So as to covalent-bind the fishing primer at the solid surface of the analysis container for a composition of the fishing probe, a nucleoLink™ strip module (NUNC Inc.), in which an operation radical is exposed, is used for forming a covalent bonding with an end of phosphorylation end of the primer. So as to, amplify the fishing probe WSV f460 which recognize 66771-67236 nucleotide portion in a genome base sequence (Yang et al., J. Virol. 75(23): 11811-11820, 2001) of the known WSSV, a reverse direction primer ts6 MHtm having a normal direction primer wssv3Xba labeled with the sequence number 1 and the sequence number 2 is designed (refer to FIG. 3). At this time, in the reverse direction primer Ts6 MHtm. 5'-end is phosphorylated for fixing on the surface of the analysis container.

100 ng of the Ts6 MHtm reverse direction primer of the sequence number 2 is diluted with 1-methyl-imidazole, pH 7.0, and 50 ul of the dilution solution and 50 ul of 1-ethyl-3-(3-dimethylaminoprophyl)-carbodiimide are added to the analysis container of the module and are reacted for above 48 hours at 50° C., and the primer is fixed at the surface of the analysis container.

As the reaction time is passed, the reaction solution is discarded, and 0.4N NaOH denature solution (0.25% Tween 20 contained) of 1.5 times volume of the reaction solution is added to the analysis container, and it is washed three times for 2 minutes at 50° C. and is washed one time for 15 minutes and is washed three times for 2 minutes. The neutralization solution (100 mMTris-HCl (pH 7.5), 150 mM NaCl, 0.1% Tween wo) of the same volume as the denature solution is inputted into the washed container and is washed three times for 15 minutes, and the primers not fixed at the surface of the analysis container are removed.

50 ul of the PCR reaction solution is inputted into the analysis container fixed with Ts6 MHtm of the sequence number 2, and PCR reaction is performed. At this time, the PCR reaction solution, is made by mixing 5 ul of 10× buffer solution, MgCl2 3.5 mM, normal direction primer Wssv3Xba 0.5 uM, reverse direction primer Ts6 MHtm 0.06 uM, mold DNA 0.5 ul (100 pg), dNTP 0.1 mM and Taq polymerization enzyme 2.5 U (Elpis Inc. Korea), and the volume is adjusted to 50 ul with the distilled water.

Here, the reverse direction primer is added to the PCR reaction solution except for the reverse direction primer fixed on the surface of the analysis container for the reason that the initial PCR amplification reaction is promoted, and the extension reaction of the fishing primer attached on the surface of the container wall is fully performed. The normal direction primer is attached more as compared to the fixed reverse direction primer, so that when the PCR reaction occurs, a lot of the fishing probe is combined as the primer fixed on the solid surface is used.

In the above reaction, the mold DNA is made by separating and purifying the 460 bp DNA piece amplified with the PCR using the normal direction primer Wssv3Xba 0.5 uM and the reverse direction primer Ts6 MHtm 0.5 um. At this time, the concentration is 200 pg/ul. The reaction solution is denatured for 1 minute at 94° C., and it is denatured for one minute at 94° C., and is annealed for 1 minute at 54° C., and the extension reaction is performed 35 times for 1 minute at 72° C. and it is amplified for 5 minutes at 72° C.

When the PCR is completed, the reaction liquid is removed from the analysis solution, and it is washed three times for 2 minutes at 55° C. using the 0.2N NaOH denature solution (0.1% Tween 20 contained) of 1.5 times volume, and is washed one time for 15 minutes and three times for minutes, and the amplified DNA is denatured from the primer fixed on the surface of the analysis container, and the fixed single strand fishing probe is remained, and the remaining strands are removed. The neutralization solution (100 mMTris-HCl (pH 7.5), 150 mM NaCl, 0.1% Tween 20) of the same volume is inputted, and it is washed three times for 15 minutes, and the remaining NaOH components are removed.

The fishing probe WSV f460 of the amplified WSSV has a base sequence labeled with the sequence number 3 as a single strand polynucleotide.

So as to remove a non-specific attaching force of the prepared module, pbluescript vector DNA (Invitrogen Inc.) of diluted 100 pg is added to 50 ul of 2× hybridization buffer solution and the blocking solution of the same amount as a non-specific DNA (blocking solution; 1% skim milk protein (w/v) 50 mM, Tris-HCl-150 mM, pH 7.4, Roche Inc.) in the analysis container, and a hybridization reaction is performed for 2 hours at 55° C.

At this time, the 2× hybridization buffer solution is manufactured by mixing 10×SSC (1.5M NaCl, 0.15M sodium citrate, pH 7.0), 0.2% sarcosine, 0.04% SDS (sodium dodecyl sulfate) and 2 mM CTAB (cetyltrimethylammonium bromide), and 2 mM CTAB is diluted with 1/50 volume using 10 mM CTAB and is separately mixed. After the hybridization reaction is completed, a hybridization buffer solution is discarded, and the analysis container is washed three times for 2 minutes at 50° C., one time for 15 minutes and 3 times for 2 minutes using 0.2N NaOH denature solution (0.1% Tween 20 contained) of 1.5 times volume, and the non-specific attaching force of the surface is removed. The prepared module is sealed and stored at 4° C. before it is used for the experiment.

The fishing probe is manufactured with respect to the Hpv in the same manner. So as to amplify the fishing probe hpv f390 which recognizes the 1805-2190 nucleotide portion in the genome base sequence (Bonami, et al., J. Gen. Virol. 76(Pt4): 813-817, 1995) of the Hpv, the normal direction primer Hpv20L labeled with the sequence number 4 and the reverse direction primer Hpv30R labeled with the sequence number 5 in which 5'-end is phosphorylated are used (refer to FIG. 4), and the amplified fishing probe has a base sequence labeled with the sequence number 6 as a single strand poly nucleotide.

[1-2] Manufacture of Reporter Probe Labeled with Tag

The reporter probe labeled with the tag which recognizes a specific gene portion different from a specific gene portion that is recognized by the fishing probe with respect to the WSSV in the [1-1] embodiment is manufactured in the following method. First, so as to amplify the reporter probe WSV p190 which recognizes the 67266-67454 nucleotide portion in the genome base sequence of the WSSV, the normal direction primer WS5Mid labeled with the sequence number 7 and the reverse direction primer WSSV5 labeled with the sequence number 8 are designed (refer to FIG. 3). As the mold DNA for a PCR reaction, the WSSV gene DNA is amplified with the PCR using the WS5Mid and the WSSV5 primers, and the amplified 190 bp DNA piece is purified with an agarose gel.

At this time, in the PCR reaction, it is denatured for 1 minute at 94° C., and it is denatured for 1 minute at 94° C. and is annealed for 1 minute at 54° C., and the extension reaction is performed 30 times for 1 minute at 72° C., and is amplified for 5 minutes at 72° C. Here, the WSSV gene DNA is not directly amplified with the PCR, but the piece amplified with the PCR is used. In the later case, it is because a reporter probe having a high purity is manufactured based on a mass production.

The PCR for a reporter probe amplification is performed using a pair of primers labeled with the sequence numbers 6 and 7 and the WSSV DNA piece, and the PCR reaction solution is made by mixing 10× buffer solution 5 ul, MgCl2 3.5 mM, normal direction primer WS5MiduM, reverse direction primer WSSV5 0.5 uM, mold DNA 0.5 ul, dNTP 0.2 mM (dTTp 0.12 mM), digoxygenin-11-dUTP (Roche Inc. (Germany) 0.08 mM and Taq polymerization enzyme 2.5 U (Elpis Inc. Korea), and the final volume is adjusted to 50 ul with distilled water. The reaction solution is denatured for 2 minutes at 94° C., and is denatured for 1 minute at 94° C., and is annealed for 1 minute at 56° C., and the extension reaction is performed 35 times for 1 minute at 72° C. and is amplified for 5 minutes at 72° C. The amplified substance is purified with 1.6% agarose gel, and the concentration is measured and is stored at 4° C. The reporter probe WSV9190 with respect to the WSSV is a double strand polynucleotide and has a base sequence labeled with the sequence number 9.

The reporter probe is manufactured with respect to the WSSV in the above method. So as to amplify the reporter probe hpv p320 which recognizes the 2243-2563 nucleotide portion in the genome sequence of the WSSV, the normal direction primer Hpvp2L labeled with the sequence number 10 and the reverse direction primer Hpvp2R labeled with the sequence number 11 are used, and the amplified reporter probe hpv 9320 is a double strand poly nucleotide and has a base sequence labeled with the sequence number 12.

Embodiment 2

Manufacture of Standard Curve for Quantitative Multiple Pathogenic Microorganisms

[2-1] Preparation of Standard Sample

So as to manufacture the standard curve using the multiple pathogenic microorganisms detection kit manufactured according to the embodiment 1 of the present invention, the DNA piece is amplified with the PCR, which includes a portion recognized by the fishing probe and the reporter probe as the standard sample with respect to the WSSV and the Hpv. As shown in FIG. 4, the standard DNA of the WSSV is amplified using the normal direction primer Wssv3xba of the sequence number 1 and the reverse direction primer of the sequence number 8 by using the WSSV genome DNA as a mold which includes the fishing probe WSV f460 recognition portion and the reporter WSV p190 recognition portion.

In addition, as shown in FIG. 5, the standard DNA of the WSSV is amplified using the Hpv20L normal direction primer of the sequence number 4 and the Hpvp2R reverse direction primer of the sequence number 11 by using the WSSV genome DNA as a mold in the s760 portion which includes the fishing probe hpv f390 recognition portion and the reporter probe hpv p320 recognition portion. At this time, the PCR reaction solution is made by mixing 10× buffer solution 5 ul, MgCl2 3.5 mM, normal direction primer 0.5 uM, reverse direction primer WSSV5 0.5 uM, mold DNA 200 pg, dNTP 0.2 mM and Taq polymerization enzyme 2.5 U (Elpis Inc. Korea), and the final volume is made with 50 ul with distilled water. The reaction solution is denatured for 2 minutes for 94° C., and is denatured for 1 minute at 94° C., and is annealed for 1 minute at 56° C., and the extension reaction is performed 35 times for 1 minute at 72° C., and is amplified for 5 minutes at 72° C.

The amplified standard sample DNA quantitatively measures the DNA amount after the purification at the agarose gel, and the mol concentration is measured, and the gene copy number is computed. As a result, the molecular quantity of the standard sample DNA of the WSSV is $4.61 \times 10^5$, and the gene copy number of 1 ng is $1.3 \times 10^9$. The molecular quantity of the standard sample DNA of the Hpv is $5.0 \times 10^5$, and the gene copy number per 1 ng is $1.2 \times 10^9$.

[2-2] Drawing of Standard Curve

The WSSV and the Hpv prepared in the [2-1] are detected using the multiple pathogenic microorganisms detection kit of the first embodiment of the present invention, and each standard curve is drawn.

The hybridization module fixed with the fishing probes with respect to the WSSV and Hpv is inserted into the fixing frame, and is washed three times for 15 minutes with neutralization solution, and the fishing probe of a dry state is hydrated, and it is activated for an easier hybridization.

The hybridization buffer, which does not include the CTAB of the same volume as 50 ul of distilled water containing 0.5% blocking solution in the activated hybridization module is added, and a preliminary hybridization is performed for 1 hour at 55° C. After the preliminary hybridization reaction is completed, the hybridization module is washed one time with 0.5×SSC (75 mM NaCl, 7.5 mM sodium citrate, pH 7.0) solution at the same temperature, and the hybridization is fully removed.

The concentration of the standard sample DNA with respect to each virus is adjusted to $1.0 \times 10^8$ copy number, and is diluted with distilled water 5 times, and a standard sample dilution solution is prepared. A reporter probe labeled with digoxygenin is added to the standard sample dilution solution, and the final volume is adjusted to 50 ul using distilled water. The mixed solution is processed for 15 minutes at 98° C. and is denatured, and is added to a hybridization module fixed with the fishing probe along with the hybridization buffer solution of the same amount which includes 0.2% blocking solution.

It is swung at 200 rpm for 2 hours at 55° C., and a hybridization reaction is performed for forming a triple composite of a fishing probe-analysis-reporter probe.

After the hybridization reaction is finished, the hybridization module is washed with a 2×SSC (300 mM NaCl, 30 mM sodium citrate, pH 7.0) solution three times at 55° C., and one time for 15 minutes with a 1×SSC (150 mM NaCl, 15 mM sodium citrate, pH7.0), and three times for 2 minutes with a 0.5×SSC (75 mM NaCl 7.5 mM sodium citrate pH7.0) for thereby removing a reaction solution.

Here, with the blocking solution, a solution made by diluting an anti-digoxygenin-peroxidase (Roche) 1000 times is added, and is reacted at a room temperature for 1 hour, so that an antigen-antibody reaction is induced. The antibody not coupled to a triple composite is washed by washing 7 times at a room temperature with a reutilization solution and is removed, and with a substrate of an enzyme connected with the antibody, a BM chemiluminecence substrate, Roche Inc. Germany of 100 ul is added and reacted for 5 minutes at a room temperature, and a color emission reaction is induced. The degree of the color emission is measured for 0.5 through 2 seconds using a luminometer, Berthod, and a relative enzyme activation is calculated.

The hybridization module that the light emission reaction is finished is washed three times for 3 minutes at 55° C. with 0.2 NaOH denature solution (0.1% Tween 20 contained) of 1.5 times volume after the reaction solution is discarded, and is washed one time for 15 minutes, and is washed for 1 hour with 0.1% sarcosine (0.1% SDS and 0.1% Tween 20 contained) solution, so that an analysis sample and reporter probe hybridized in the fishing probe are removed, and the modules are reused for an analysis of other samplers.

As a result, as shown in FIGS. 7 and 8, the multiple pathogenic microorganisms detection kit made according to an embodiment 1 of the present invention is able to quantitatively detect the WSSV and Hpv standard sample DNA.

As shown in FIGS. 7 and 8, the measurement values of the standard curve are regression-analyzed, and the regression curve equation is obtained, and the measurement values of each sample is inputted into the equation, so that the gene copy number of the actually infected virus can be computed.

Embodiment 3

Detection and Ration of the Multiple Pathogenic Microorganisms Using a Standard Curve The WSSV and Hpv with respect to the actual samples are quantitatively measured using the kit of the embodiment 1 of the present invention with the help of the standard curve made in the embodiment 2.

First, the penaeus chinensis and samples not having the WSSV and Hpv in their outer symptoms are randomly selected and tested.

The legs of the penaeus chinensis are chopped by 50 mg, and are inputted into the microfuge tube, and 50 ul of an analysis enzyme buffer solution (30 mM Tris-HCl, 10 mM EDTA, 1% SDS) containing a protein decomposition enzyme K (Proteinase K) of 500 ug/ml is added, and is reacted for 3 hours at 50° C. The reaction solution is centrifugal-processed for 5 minutes at 15000 rpm, and a supernatant is obtained and mixed with 100% ethanol of two times volume, and a gene substance is deposited, and it is dissolved in 500 ul of distilled water. The portions (deposited protein) not dissolved in the distilled water are centrifugal-separated, and removed.

The thusly prepared samples are mixed with the reporter probe labeled with digoxygenin based on the method of the embodiment 2 and is added to the hybridization module fixed with the fishing probe, and the hybridization reaction is performed, and the light emission degree is measured based on the color emission reaction.

The regression curve equations are obtained from the standard curves of FIGS. 7 and 8 made using the standard samples of the WSSV and Hpv (refer to FIG. 9).

1) WSSV Regression Curve $$F(x)=7.63e+5xx/(1-6.192e-3xx)$$

2) HPV Regression Curve $$F(x)=7.45e+5xx/(1-6.28e-3xx)$$

In the above equations, "x" is a variable, namely, a relatively activity. The relative enzyme activation value of actual sample measured using the detection kit of the present invention is inputted into the regression curve equation, and the viruses infected to each sample are quantitatively measured (FIG. 10). Assuming that the standard samples (E8 standard) of the $10 \times 10^8$ copy number of the HPV and WSSV are 100% and assuming that the distilled water sample (negative comparison group) is 0% activity, the measurement values of the samples and the computation values obtained by inputted into the equations are shown in the Table 1.

TABLE 1

| Samples | HPV Measurement Values(%) | HPV Virus copy numbers | WSSV Measurement values(%) | WSSV Virus copy numbers |
|---|---|---|---|---|
| E8 standard | 100 | 2.0e+8 | 100 | 2.0e+8 |
| GR1 | 0.61 | Out of measurement scope | 12 | 9.6e+6 |
| GR2 | 0.62 | Out of measure0nt scope | 83 | 1.3e+8 |
| Lab82 | 2.7 | 2.0e+6 | 2.6 | 2.0e+6 |
| Lab81 | 2.7 | 2.0e+6 | 0.8 | 6.1e+5 |
| KC22 | 2.4 | 1.8e+6 | 0.63 | Out of measurement scope |
| KC21 | 29 | 2.6e+7 | 1.5 | 1.1e+6 |

As seen in the above table 1, in the GR1 and GR2 samples, the WSSV are detected with about $1.0 \times 10^7$ through $10^6$ copy numbers, and in the same samples, the HPV is less detected with $6.0 \times 10^5$ copy numbers.

However, in the KC21 samples, the HPV is strongly detected with $4.0 \times 10^7$ copy numbers, and the WSSV is weakly detected with $2.2 \times 10^6$ copy numbers. From a result, it is known that the detection kit according to the present invention is able to selectively detect a corresponding virus from the actual samples.

Embodiment 4

Detection of Tobacco Mosaic Virus (TMV) and Beet Curly Top Virus (BCTV)

[4-1] Manufacture of Standard Curve

So as to detect the TMA and BCTV using a microorganism detection kit according to the present invention, a hybridization module fixed with a fishing probe 415 bp of the sequence number 15 using a normal direction primer TMV-415F of the sequence number 13 which recognizes 5829 through 5848 nucleotide portion and a reverse direction primer TMV-415 of the sequence number 14 which recognizes 6217 through 6243 nucleotide portion in the known TMV in the known method, and a hybridization module fixed with the fishing probe 288 bp of the sequence number 18 using a normal direction primer BCTC-4L of the sequence number 16 which recognizes 858 through 877 nucleotide portion and a reverse direction primer BCTC-4PR of the sequence number 17 which recognizes 1123 through 1145 nucleotide portion in the genome sequence (GenBank registered number: NC_001412) of the known BCT.

In the same method as [1-2] of the embodiment 1 of the present invention, a reporter probe 1 (256 bp) of the sequence number 21 is prepared using a normal direction primer TMV-NF of the sequence number 19 which recognizes 5102 through 5121 nucleotide portion and a reverse direction primer TMV-NR of the sequence number 20 which recognizes 5338 through 5357 nucleotide portion in the genome base sequence of the TMV and a reporter probe 2 (173 bp) of the sequence number 24 is prepared using a normal direction primer TMA-2F173 of the sequence number 22 which recognizes 5591 through 5610 nucleotide portion and a reverse direction primer TMV-173R of the sequence number 23 which recognizes 5745 through 5764 nucleotide portion.

In addition, a reporter probe 218 bp of the sequence number 27 is prepared using a normal direction primer BCTV-RF of the sequence number 25 which recognizes 1300 through 1319 nucleotide portion and a reverse direction primer BCTV-PR of the sequence number 26 which recognizes 1498 through 1518 nucleotide portion in the genome sequence of the BCTV.

At this time, two reporter probes are manufactured for recognizing different portions so as to increase a detection sensitivity with respect to the TMV.

For a standard sample DNA of the TMV, a TMV RNA gene of 6395 bases are reverse-transcripted using a reverse direction primer TMV-415 of the sequence number 14 for thereby preparing cDNA, and it is amplified with PCR using a normal direction primer TMV-NF of the sequence number 19 and a reverse direction primer TMV-415RP of the sequence number 14. Namely, for the same, a DNA piece (5102 through 6243 nucleotide portions corresponding to TMVgp4, gp5 and gp6) is used. For the standards sample DNA of the BCTC which is a single strand DNA virus, a DNA piece of a 660 bp amplified with the PCR using a normal direction primer BCTC-4L of the sequence number 16 and a reverse direction primer BCTC-RP of the sequence number 26 with respect to 858 through 1518 nucleotide portion corresponding to the BCTVgp4 in the BCTV of 2994 bases is used, and the concentration of the standard sample is continuously diluted with 109 through 106.

The PCR reaction condition and the composition of the reaction solution are the same as the embodiment 1 of the present invention.

Each standard curve is made by detecting the standard sample DMA of the TMV and BCTV using a hybridization module fixed with a fishing probe and a reporter probe. As a result, as shown in FIG. 11, the standard sample of the TMV has a regression curve with an equation of $f(x) 6.89e5xx/(1-3.14e-3xx)$, and the curve has a measurement value and a relational coefficient of $R=0.999978$ and $Rsqr=0.999957$. The standard sample of the BCTV has a regression curve with an equation of $f(x) 9.37e+5xx/(1-6.53e-4xx)$. The curve has a measurement value and a relationship of $R=0.999963$ and $Rsqr=0.999926$.

In the equation, x is a variable, namely, a relative activity.

The leaves of the tobacco infected with the detection TMV and the BCTV are collected and dried, and the virus numbers are measured from the samples based on the [4-2] standard curve.

The samples are smashed by adding 1 ml of PBS per a dried sample of 100 ug, and the extract of about 2 ul is analyzed using the detection kit of [4-1] of the embodiment 4, and the viruses infected to each sample are measured from each standard curve.

At this time, for the positive comparison group, the TMV $1 \times 10^8$ copy numbers (TMV 1F+8) and the BCTC $1 \times 10^8$ copy numbers (BCTC1E+8) are used and they are used as a negative comparison group. In the following table 2, "not detected" means a non-detection since it is out of the lower limit of the standard curve, and "out of the scope" means an out of the scope of the upper limit.

TABLE 2

| Samples | Reverse value of virus measured in TMV module | samples | Reverse value of virus measured in BCTV module |
|---|---|---|---|
| TMV1 | 2.29e+7 | BCTV1 | 4.53e+8 |
| TMV2 | 2.18e+7 | BCTV2 | 1.59e+6 |
| TMV3 | 7.85e+6 | BCTV3 | Out of scope |
| TMV 1E+8 | 1.00e+8 | BCTV 1E+8 | 1.00e+8 |
| TMV 1E+8 | Not detected | TMV 1E+8 | Not detected |

As seen in the above table 2, in the hybridization module for detecting the TMV, the BCTV1E+8 is not detected, and in the hybridization module for detecting the BCTV, TMV1E+8 is not detected. It means that each hybridization module is specific to the TMV and the BCTV.

For each sample, in the TMV, $6.28 \times 10^5$ through $4.53 \times 10^7$ viruses are detected in the valid scope, and in the BCTV, $1.59 \times 10^6$ through $2.29 \times 10^7$ viruses are detected in the valid scope.

In the BCTV3 sample, the number of the viruses is out of the valid scope, so that it is measured below the detection sensitivity. In addition, the BCTV of the single strand DNA virus (ss DNA virus) and the TMV of the single strand RNA virus (ss RNA virus) are detected in the valid measurement scope, so that it means that the detection kit of the present invention is able to effectively detect the double strand DNA gene as well as the single strand DNA gene and the single strand RNA gene.

Embodiment 5

Detection of Rock Bream Iridovirus (RBIV)

So as to detect the RBIV which causes mass deaths of rock bream using the microorganism detection kit of the present invention of [5-1] standard curve, a hybridization module fixed with a fishing probe is prepared with respect to the major capsid protein (MCP) of 1,362 bp in the gene of the RBIV. First, in the same method as [1-1] of the embodiment 1, a hybridization module fixed with a fishing probe 408 bp is manufactured using a normal direction primer MCP 408F of the sequence number 28 which recognizes 729 through 748 nucleotide portion and a reverse direction primer MCP 408 of the sequence number 29 which recognizes 1108 through 1136 nucleotide portion in the base sequence (GenBank registered number: AB109371) of the genome MCP gene of the RBIV. In addition, a reporter probe 282 bp of the sequence number 33 is prepared using a normal direction primer MCP282F of the sequence number 31 which recognizes 216 through 235 nucleotide portion and a reverse direction primer MCP282R of the sequence number 32 which recognizes 478 through 497 nucleotide portion in the base sequence of the RBIV.

For the standard sample DNA for the RBIV detection, a DNA piece of 920bo amplified with PCR using a normal direction primer MCP292F of thee sequence number 31 and a reverse direction primer MCP408 of the sequence number 29 with respect to the 216 through 1136 nucleotide portion in the MCP genes of 1362 bp. The concentration of the standard DNA is used by continuously diluting 109 through 106. The PCR reaction condition and the composition of the reaction solution are the same as the embodiment 1.

As shown in FIG. 13, as a result of the standard curve made by detecting the standard sample DNA of the RBIV MCP gene using the hybridization module fixed with a fishing probe and a reporter probe, the standard sample DNA has a regression curve with an equation of $f(x)=5.3exx/(1-4.72-3xx)$, and the curve has a measurement value and a relational coefficient of $R=0.999986$ and $Rsqr=0.999972$.

[5-2] Detection of RBIV Using Standard Curve

The tissue of 20 mg is taken from liver and spleen of the rock bream and is homogenized in 150 ul of STE buffer solution (1.0% SDS, 30 mM Tris-Cl (pH 8.0), 10 mMEDTA), and a protein decomposition enzyme K (Proteinase K, 500 ug/ml) is added, and the tissue is decomposed for three hours.

The above reaction solution is centrifugal-separated at 15000 rrpm for 5 minutes, and supernatant is separated, and 20 ul of the separated supernatant is used for a virus gene measurement. At this time, for the standard sample, RBIB MCP gene $1 \times 10^8$ copy (1E+8) is used.

TABLE 3

| Samples | RBIV MCP gene copy number |
| --- | --- |
| 1E+8 standard | 1.00e+8 |
| Liver sample 1 | 7.18e+6 |
| Spleen sample 1 | 3.09e+8 |
| Liver sample 2 | Out of scope |
| Spleen sample 2 | 2.21e+7 |
| Liver sample 3 | Out of scope |
| Spleen sample 3 | 1.31e+8 |

As seen in the table 3, the RBIV is generally found more in the spleen than in the liver. According to the infection step, it may be found more in the liver (FIG. 14). As a result, since the detection kit of the present invention is able to specifically detect the RBIV MCP gene, according to the infection step of the virus, it is possible to analyze the spreading aspect of the infection of the virus based on the organ of the fish.

Embodiment 6

Detection of Penaeus Chinensis

[6-1] Drawing of Standard Curve

So as to check whether the detection kit of the present invention can be adapted to a gene detection of a multiple cell organism, a hybridization module fixed with a fishing probe and a reporter probe are prepared with respect to CHH/GIH/MIH (Crustachean Hyperglycemic Hormone [CHH]/Gonad Inhibiting Hormone [GIH]/Molt-Inhibiting Hormone[MIH] which is able to control the growth in the penaeus chinensis. First, a hybridization module fixed with a fishing probe 285 bp of the sequence number 36 is prepared using a normal direction primer Pem-5 of the sequence number 34 which recognizes 231 through 250 nucleotide portion and a reverse direction primer Pem300RP of the sequence number 35 which recognizes 496 through 515 nucleotide portion in the 907 bp base sequence (GenBank registered number: AY346378) of the penaeus chinensis CHH/GIH/MIH gene in the same method as [1-1] of the embodiment 1.

In addition, a reporter probe 1 (165 bp) of the sequence number 39 is prepared using a normal direction primer Pem-CL of the sequence number 37 which recognizes 14 through 33 nucleotide portion and a reverse direction primer Pem-2R165b of the sequence number 38 which recognizes 162 through 180 nucleotide portion in the base sequence of the penaeus chinensis CHH/GIH/MIH gene in the same method as [1-2] of the embodiment 1, and a reporter probe 2 (137 bp) of the sequence number 42 is prepared using a normal direction primer Pem-R602F of the sequence number 40 which recognizes 602 through 623 nucleotide portion and a reverse direction primer Pem-3 of the sequence number 41 which recognizes 717 through 736 nucleotide portion.

For the standard sample DNA for a CHH/GIH/MIH gene detection, a DNA piece amplified with PCR using a normal direction primer Pem-CL of the sequence number 37 and a reverse direction primer Pem-3 of the sequence number 41 is used with respect to 14 through 736 nucleotide portion in the CHH/GIH/MIH gene of a size of 907 bp. The concentration of the standard sample DNA is continuously diluted with 109 through 106. The PCR reaction condition and the reaction solution composition are same as the embodiment 1.

As a result of the drawing of the standard curve by detecting the standard sample DNA of the CHH/GIH/MIH of the penaeus chinensis using a hybridization module fixed with a fishing probe and a reporter probe, as shown in FIG. 15, the standard sample DNA has a regression curve with an equation of $f(x)=6.21e5xx/(1-3.80e-3xx)$, and the curve has a measurement value and correlation coefficient of $R=0.999997$ and $Rsqr=0.999994$.

[6-2] Detection and Measurement of Neuron Hormone Gene Using Standard Curve 100 mg of tissue is taken from liver pancreas and leg of the penaeus chinensis and is homogenized in 500 ul of STE buffer solution (10% SDS, 30 mM Tris, 1 mMEDTA), and a protein decomposition enzyme K (500 ug/ml) is added, and it is reacted for 3 hours, and the tissue is decomposed. The reaction solution is centrifugal-processed at 15000 rpm for 5 minutes, and the supernatant is separated, and is purified with phenol and chloroform, and the gene DNA of the penaeus chinensis is obtained.

The obtained gene DNA is dissolved in distilled water of 500 ul, and 50 ul of the same is used for a detection of the CHH/GIH/MIH.

TABLE 4

| Samples | DNA concentration(ng/ul) | CHH/GIH/MIH gene copy numbers of *penaeus chinensis* |
|---|---|---|
| 1E+8 standard | | 1.00e+8 |
| GR1 | 360 | 4.65e+5 |
| GR2 | 205 | Out of scope |
| PP2 | 160 | Out of scope |
| HP2 | 388 | 5.98e+5 |
| PP3 | 499 | 9.68e+5 |
| HP3 | 210 | Out of scope |

As a result, as seen in the table A the CHH/GIH/MIH gene is measured in a scope of $5\times10^5$ through $1\times10^6$ in proportion to the amount of the DNA amount in each sample as shown in FIG. 16. This result means that the detection method using a hybridization module of the present invention can be used for detecting virus or bacteria as well as genes of multiple cell organism having a large size gene.

In addition, the detection method of the present invention may be used for a detection of a genetically modified organism (GMO) which needs a faster test of a plurality of samples.

Embodiment 7

Detection of *Vibrio Vulnificus*

[7-1] Drawing of Standard Curve

So as to detect *Vibrio vulnificus* which is a virus of septicemia, a hybridization module fixed with a fishing probe and a reporter probe are made with respect to toxic cytolysin gene in the entire genes of the viruses.

First, in the same method as [1-1] of the embodiment 1, a hybridization module fixed with a fishing probe 383 bp of the sequence number 45 is prepared using a normal direction primer Vvh383F of the sequence number 43 which recognizes 399 through 428 nucleotide portion and a reverse direction primer Vvh383 of the sequence number 44 which recognizes 752 through 781 nucleotide portion in the base sequence (GenBank registered number: M34670) of the cytolysin gene of the *Vibrio vulnificus* 2237 bp. In addition, a reporter probe 241 bp of the sequence number 48 is prepared using a normal direction primer Vvh266F of the sequence number 46 which recognizes 1263 through 1282 nucleotide portion and a reverse direction primer Vvh428R of the sequence number 47 which recognizes 1484 through 1503 nucleotide portion in the base sequence of the *vibrio vulnificus* cytolysin gene in the same method as [1-2] of the embodiment 1.

For the standard sample 1503 portion for a cytolysis gene detention, a DNA piece of 1100 bp amplified with PCR using a normal primer Vvh383F of the sequence number 43 and a reverse direction primer Vvh428R of the sequence number 428 is used. The DNA concentration of the standard sample is continuously diluted with 109 through 106 and is used. The PCR reaction condition and the composition of the reaction solution are the same as the embodiment 1.

For the DNA, as a result of the drawing of the standard curve by detecting a standard sample DNA of the cytolysis of *Vibrio vulnificus* using the hybridization module fixed with a fishing probe and a reporter probe in the cytolysin of 2237 bp size, as shown in FIG. 17, the standard sample DNA of the *Vibrio vulnificus* has a regression curve with an equation of $f(x)=9.16e5xx/(1=8.67e=4xx)$, and the curve has a measurement value and a relational coefficient of $R=0.999988$ and $Rsqr=0.999976$.

[7-2] Detection of *Vibrio Vulnificus* Using Standard Curve

*Vibrio vulnificus* and *Vibrio parahaemolyticus* is provided in a marine broth of 2 ml and is cultivated all nights at 30° C., and bacteria is obtained after centrifugal process. 600 ml of decomposition solution (0.5% SDS, 100 ug/ml protein decomposition enzyme K) is added, and it is reacted for 3 hours, and the tissue is decomposed. The reaction solution is added by 100 ul of 5M NaCl solution (last concentration 0.7 MnaCl) and 80 ul of CTAB/NaCl solution (last concentration 10% CTAB, 0.7M NaCl), and it is reacted for 10 minutes at 65° C., and phenol:chloroform:isoamylalcohol (25:24:1) are processed two times, and the gene DNA of the bacteria is obtained. The DNA is dissolved in the TE buffer solution of 100 ul, and the test is performed.

As a result of the measurement of the cytolysis using a detection kit of [7-1] of the embodiment 7 and the standard curve with respect to 20 ml of *Vibrio vulnificus* and *Vibrio papahaemolyticus* DNA sample, the genes of about $3\times10^7$ copy numbers are measured in *Vibrio vulnificus*, and a measurement value out of the valid measurement scope is obtained in the sample of *Vibrio papahaemolyticus* as shown in FIG. 18. With the above results, the hybridization module of the present invention is able to specifically detect *Vibrio vulnificus* and *Vibrio papahaemolyticus*, and is used for recognizing genetically similar viruses.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. A kit for detecting multiple pathogenic microorganisms comprising a hybridization module fixed with a fishing probe, a reporter probe labeled with a tag, a standard sample, a hybridization buffer solution, a washing solution, a denature solution, a neutralization solution, an antibody dilution solution, an enzyme linked anti-Tag antibody and a substrate solution of the enzyme, wherein the fishing probe is a single stranded polynucleotide designed to recognize one portion of a specific gene of the microorganism to be detected; the reporter probe is a double stranded polynucleotide designed to recognize the other portion of the specific gene which does not overlap with the portion recognized by the fishing probe;

said denature solution consists essentially of 0.2 to 0.4N NaOH solution containing a 0.1 through 0.25% Tween 20; said neutralization solution contains 75 to 125 mM Tris-HCl (pH7.5), 125 to 175 mM NaCl and 1 to 2% Tween 20; and said antibody dilution solution contains 1% skim milk protein (w/v), 50 mM Tris-HCl (pH7.4) and 150 mM NaCl.

2. The kit of claim 1, wherein said standard sample is an amplified DNA which is adapted to include the specific gene portion recognized by the fishing probe and the specific gene portion recognized by the reporter probe by using a gene of a pathogen to be detected as a template.

3. The kit of claim 1, wherein said fishing probe is covalent-bonded on an inner surface of the hybridization module.

4. The kit of claim 1, wherein said tag labeled on the reporter probe is selected from the group consisting of digoxygenin, biotin, fluorescein and radioactive isotope.

5. The kit of claim 1, wherein said hybridization buffer solution consists essentially of 10×SSC (1.5M NaCl, 0.15M sodium citrate, pH 7.0), 0.2% of sarcosine, 0.04% SDS(Sodium docecyl sulfate), 0.2% of blocking solution (0.2% skim milk protein (w/v) 50 mM, Tris-HCl 150 mM, pH 7.4) and 1 to 4 mM CTAB (cetyltrimethylmmonium bromide).

6. The kit of claim 1, wherein said washing solution consists essentially of a 0.5× to 2×SSC (75 to 300 mM NaCl, 7.5 to 30 mM sodium citrate, pH7.0) solution.

7. The kit of claim 1, wherein the enzyme of said enzyme linked anti-Tag antibody is selected from the group consisting of horseradish peroxidase, alkaline phosphatase, and β-galactosidase, and a substrate of said enzyme is selected from the group consisting of luminol, 4-nitrophenyl phosphate, CSPD (Disodium 3-(4-methoxyspiro 1,2-dioxetane-3,2-(5-chloro) tricycle[3.3.1.13,7]decan-4-yl)phenyl phosphate), and X-gal (5-bromo-4-chloro-3-indolyl-beta-d-galactoside).

8. A method for quantitatively detecting multiple pathogenic microorganisms using the kit of claim 1, comprising: 1) a step in which a fishing probe fixed at a hybridization module is activated; 2) a step in which an analysis sample, a reporter probe and a hybridization buffer solution is added to the hybridization module, and a hybridization reaction is induced, and a triple composite of a fishing probe-analysis sample-reporter probe is formed; 3) a step in which the amount of the triple composite is measured using an ELISA; and 4) a step in which the hybridization module is washed and recycled, wherein in said step 1), the hybridization module is washed using a neutralization solution consisting essentially of 75 to 125 mM Tris-HCl (pH7.5), 125 to 175 mM NaCl and 1 to 2% Tween 20; and said step 2) includes: a step in which in said hybridization reaction, the analysis sample and the reporter probe labeled with the tag are mixed and denatured for 10 to 20 minutes at 95 to 100° C.; a step in which said denatured mixture is added to the hybridization module fixed with the fishing probe along with the amount of hybridization buffer solution equal to the denature solution; and a step in which the hybridization module is agitated for 1 to 3 hours at 50 to 55° C.

9. The method of claim 8, further comprising a preliminary hybridization step before the hybridization reaction of the step 2).

10. The method of claim 9, wherein a equal amount of volume of the hybridization buffer solution as a distilled water containing 0.3% blocking solution is added to the hybridization module of the step 1), and said hybridization reaction is performed for 0.5 to 2 hours at 50 to 55° C.

11. The method of claim 10, wherein said hybridization buffer solution used for the preliminary hybridization reaction does not contain CTAB.

12. The method of claim 10, wherein the hybridization reaction is performed after washing the module that completes the preliminary hybridization reaction with a washing solution at 50 through 55° C.

13. The method of claim 12, wherein said washing is performed one time using a 0.5×SSC (75 mM NaCl, 7.5 mM sodium citrate, pH7.0) solution.

14. The method of claim 8, wherein said analysis sample is prepared by the steps of: a step in which an organism sample used for detecting infections of pathogens is chopped or homogenized; a step in which a protein decomposition enzyme K (proteinase K) is processed for 1 to 3 hours at 37 to 50° C.; and a step in which a supernatant is obtained by centrifugal which separates the obtained reaction solution.

15. The method of claim 8, wherein the module processed via the hybridization reaction of the step 2 is washed at 50 to 55° C. to remove a non-reacted substance.

16. The method of claim 15, wherein said hybridization module is washed three times for 2 minutes with a 2×SSC (300 mM NaCl, 30 mM sodium citrate, pH 7.0) solution, and is washed one time for 15 minutes with a 1×SSC (150 mM NaCl, 15 mM sodium citrate, pH 7.0) solution, and is washed three times for 2 minutes with a 0.5×SSC (75 mM NaCl, 7.5 mM sodium citrate, pH 7.0) solution.

17. The method of claim 8, wherein said ELISA analysis of the step 3 includes: a step in which the module that completes the hybridization reaction is washed with a washing solution at 50 to 55° C.; a step in which an enzyme linked anti-Tag antibody which recognizes the tag of the reporter probe is added in a triple composite, and it is reacted for 1 to 3 hours at 20 to 25° C., and an antigen-antibody reaction is induced; a step in which a non-bonded antibody is washed with a neutralization solution and is removed; a step in which a substrate of an enzyme linked with the antibody is added, and a color emission reaction is induced; a step in which an enzyme activation is confirmed by measuring a color emission degree; and a step in which an enzyme activation measured with each analysis sample is compared with a standard curve obtained from the standard sample for thereby determining the titer of pathogens.

18. The method of claim 8, wherein a 0.2N NaOH denature solution comprising Tween 20 of 1.5 times volume is added to the hybridization module of the step 4, and it is washed three times for 3 minutes at 50 to 60° C. and is washed one time for 15 minutes and then is washed for one hour with a 0.1% CTAB solution at the same temperature and is washed for one hour with a 0.2% sarcosine solution comprising 0.1% SDS and 0.1% Tween 20, so that the analysis sample and reporter probe hybridized to the fishing probe are removed for thereby recycling the hybridization module.

* * * * *